United States Patent
Childs et al.

(10) Patent No.: US 12,188,005 B2
(45) Date of Patent: *Jan. 7, 2025

(54) NK CELLS WITH AN INCREASED ANTIBODY-DEPENDENT CELLULAR TOXICITY (ADCC) AGAINST TUMORS

(71) Applicant: The United States of America, as represented by the Secretary, Dept. of Health and Human Services, Bethesda, MD (US)

(72) Inventors: Richard W. Childs, Bethesda, MD (US); Mattias C. V. Carlsten, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1087 days.

This patent is subject to a terminal disclaimer.

(21) Appl. No.: 16/985,797

(22) Filed: Aug. 5, 2020

(65) Prior Publication Data

US 2020/0360436 A1 Nov. 19, 2020

Related U.S. Application Data

(62) Division of application No. 15/525,921, filed as application No. PCT/US2015/060646 on Nov. 13, 2015, now Pat. No. 10,813,952.

(60) Provisional application No. 62/079,975, filed on Nov. 14, 2014.

(51) Int. Cl.
| | | |
|---|---|---|
| A61K 35/17 | (2015.01) | |
| A61K 39/00 | (2006.01) | |
| A61K 39/395 | (2006.01) | |
| A61K 45/06 | (2006.01) | |
| A61P 35/00 | (2006.01) | |
| C07K 14/715 | (2006.01) | |
| C07K 14/735 | (2006.01) | |
| C07K 16/28 | (2006.01) | |
| C12N 5/0783 | (2010.01) | |

(52) U.S. Cl.
CPC .... *C07K 16/2896* (2013.01); *A61K 39/39558* (2013.01); *A61K 39/4613* (2023.05); *A61K 39/464402* (2023.05); *A61K 39/464421* (2023.05); *A61K 45/06* (2013.01); *A61P 35/00* (2018.01); *C07K 14/70535* (2013.01); *C07K 14/7158* (2013.01); *C07K 16/2887* (2013.01); *C12N 5/0646* (2013.01); *A61K 2039/505* (2013.01); *A61K 2039/545* (2013.01); *A61K 2039/57* (2013.01); *A61K 2039/572* (2013.01); *A61K 2239/48* (2023.05); *C07K 2317/21* (2013.01); *C07K 2317/24* (2013.01); *C07K 2317/54* (2013.01); *C07K 2317/55* (2013.01); *C07K 2317/732* (2013.01); *C12N 2501/21* (2013.01); *C12N 2501/2302* (2013.01); *C12N 2501/599* (2013.01); *C12N 2510/00* (2013.01)

(58) Field of Classification Search
None
See application file for complete search history.

(56) References Cited

U.S. PATENT DOCUMENTS

| | | |
|---|---|---|
| 10,106,620 B2 | 10/2018 | Childs et al. |
| 11,293,010 B2 * | 4/2022 | Childs ................. C12N 5/0068 |
| 2015/0139943 A1 | 5/2015 | Campana et al. |

FOREIGN PATENT DOCUMENTS

| | | |
|---|---|---|
| WO | WO 2011/053322 A1 | 5/2011 |
| WO | WO 2015/195555 A1 | 12/2015 |
| WO | WO 2015/195556 A1 | 12/2015 |

OTHER PUBLICATIONS

Sanchez et. al. (J. Hematol. Oncol. 2016, 9:51, pp. 1-8) (Year: 2016).*
De Weers et. al. (J. Immunol. 2011, 186: 1840-1848) (Year: 2011).*
Roeven et. al. (Human Vaccines & Immunotherapeutics, 2013, 10(4): 896-910) (Year: 2013).*
Lundqvist et. al. (Blood, 2009, 113: 6120-6127) (Year: 2009).*
ATCC TIB-208 (2023, pp. 1-6) (Year: 2023).*
Calabretta and Carlo-Stella (Cells, 2020, 9(4): 802, pp. 1-21) (Year: 2020).*

(Continued)

Primary Examiner — Michael Szperka
Assistant Examiner — Marianne Dibrino
(74) Attorney, Agent, or Firm — Klarquist Sparkman, LLP

(57) ABSTRACT

Disclosed herein are modified NK cells, compositions comprising modified NK cells, and methods for treating a tumor or hyperproliferative disease in a subject. In some embodiments, the modified NK cells include NK cells including a heterologous nucleic acid molecule encoding a CD16 protein comprising a valine at amino acid position 158 (CD16-V158), a heterologous nucleic acid molecule encoding a CCR7 protein, or both. In some embodiments, methods include treating a subject with a tumor by administering a composition comprising an anti-cancer monoclonal antibody and administering a composition comprising the modified NK cells to the subject. Also disclosed are methods of making modified NK cells by obtaining a population of NK cells from a subject and transfecting the population of NK cells with a heterologous nucleic acid molecule encoding CD16-V158, a heterologous nucleic acid molecule encoding a CCR7 protein, or both.

14 Claims, 11 Drawing Sheets
Specification includes a Sequence Listing.

(56) References Cited

OTHER PUBLICATIONS

Animal Medical Center of Southern California, "Multiple myelomas or plasma cell myeloma is a neoplasm of well differentiated B cell lymphocytes typically originating from the bone marrow," 9 pages, 2019.
Binyamin et al., "Blocking NK Cell Inhibitory Self-Recognition Promotes Antibody-Dependent Cellular Cytotoxicity in a Model of Anti-Lymphoma Therapy," *J. Immunol.*, vol. 180, pp. 6392-6401, 2008.
Carlsten et al., "Clinical-Grade mRNA Electroporation of NK Cells: A Novel and Highly Efficient Method to Genetically Reprogram Human NK Cells for Cancer Immunotherapy," *Blood*, vol. 124, No. 21, 2153, 2014 (3 pages, Abstract).
Carlsten et al., "Genetic Manipulation of NK Cells for Cancer Immunotherapy: Techniques and Clinical Implications," *Frontiers in Immunology*, vol. 6, Article 266, 2015 (9 pages).
Childs et al., "Bringing natural killer cells to the clinic: ex vivo manipulation," *Hematology Am. Soc. Hematol. Educ. Program*, vol. 2013, pp. 234-246, 2013.
Childs et al., "Therapeutic approaches to enhance natural killer cell cytotoxicity against cancer: the force awakens," *Nature Reviews Drug Discovery*, vol. 14, No. 7, pp. 487-498, 2015.
De Weers et al., "Daratumumab, a Novel Therapeutic Human CD38 Monoclonal Antibody, Induces Killing of Multiple Myeloma and Other Hematological Tumors," *J. Immunol.*, vol. 186, pp. 1840-1848, 2011.
Harada et al., "Superior antitumor activity of trastuzumab combined with capecitabine plus oxaliplatin in a human epidermal growth factor receptor 2-positive human gastric cancer xenograft model," *Mol. Clin. Oncol.* vol. 3, pp. 987-994, 2015.
Hatjiharissi et al., "Increased natural killer cell expression of CD16, augmented binding and ADCC activity to rituximab among individuals expressing the FcγRIIIa-158 V/V and V/F polymorphism," *Blood*, vol. 110, No. 7, pp. 2561-2564, 2007.
Hermanson et al., "Utilizing chimeric antigen receptors to direct natural killer cell activity," *Frontiers in Immunology*, vol. 6, Article 195, 2015 (6 pages).
James et al., "Combination Immune Therapies to Enhance Anti-Tumor Responses by NK Cells," *Frontiers in Immunology*, vol. 4, Article 481, 2013 (12 pages).
Kudo et al, "T Lymphocytes Expressing a CD16 Signaling Receptor Exert Antibody-Dependent Cancer Cell Killing," *Cancer Research*, vol. 74, No. 1, pp. 93-103, 2013.
Li et al., "Expression of chimeric antigen receptors in natural killer cells with a regulatory-compliant non-viral method," *Cancer Gene Therapy*, vol. 17, pp. 147-154, 2010.
Liu et al., "Asymmetrical Fc Engineering Greatly Enhances Antibody-dependent Cellular Cytotoxicity (ADCC) Effector Function and Stability of the Modified Antibodies," *J. Biol. Chem.*, vol. 289, No. 6, pp. 3571-3590, 2014.
Locke et al., "Immunotherapy strategies for multiple myeloma: the present and the future," *Immunotherapy*, vol. 5, No. 9, pp. 1005-1020, 2013 (27 pages, Author Manuscript version).
Lokhorst et al, "Phase I/II does-escalation study of daratumumab in patients with relapsed or refractory multiple myeloma," *Journal of Clinical Oncology*, vol. 31, pp. 15s, 2013 (2 pages).
Lwin et al., "Preclinical animal models of multiple myeloma," *BoneKey reports*, vol. 5, Article 772, 2016 (9 pages).
Ravetch et al., "Alternative membrane forms of FcγRIII(CD16) on human natural killer cells and neutrophils," *J. Exp. Med.*, vol. 178, pp. 481-497, 1989.
Shook et al., "Natural Killer Cell Engineering for Cellular Therapy of Cancer," *Tissue Antigens*, vol. 78, No. 6, pp. 409-415, 2011 (12 pages, Author Manuscript version).
Somanchi et al., "Engineering lymph node homing of ex vivo-expanded human natural killer cells via trogocytosis of the chemokine receptor CCR7," *Blood*, vol. 119, No. 22, 5164-5172, 2012.
Stevenson et al., "Preliminary Studies for an Immunotherapeutic Approach to the Treatment of Human Myeloma Using Chimeric Anti-CD38 Antibody," *Blood*, vol. 77:1071-1079, 1991.
Veeramani et al., "Rituximab infusion induces NK activation in lymphoma patients with the high-affinity CD16 polymorphism," *Blood*, vol. 118, No. 12, 3347-3349, 2011.

\* cited by examiner

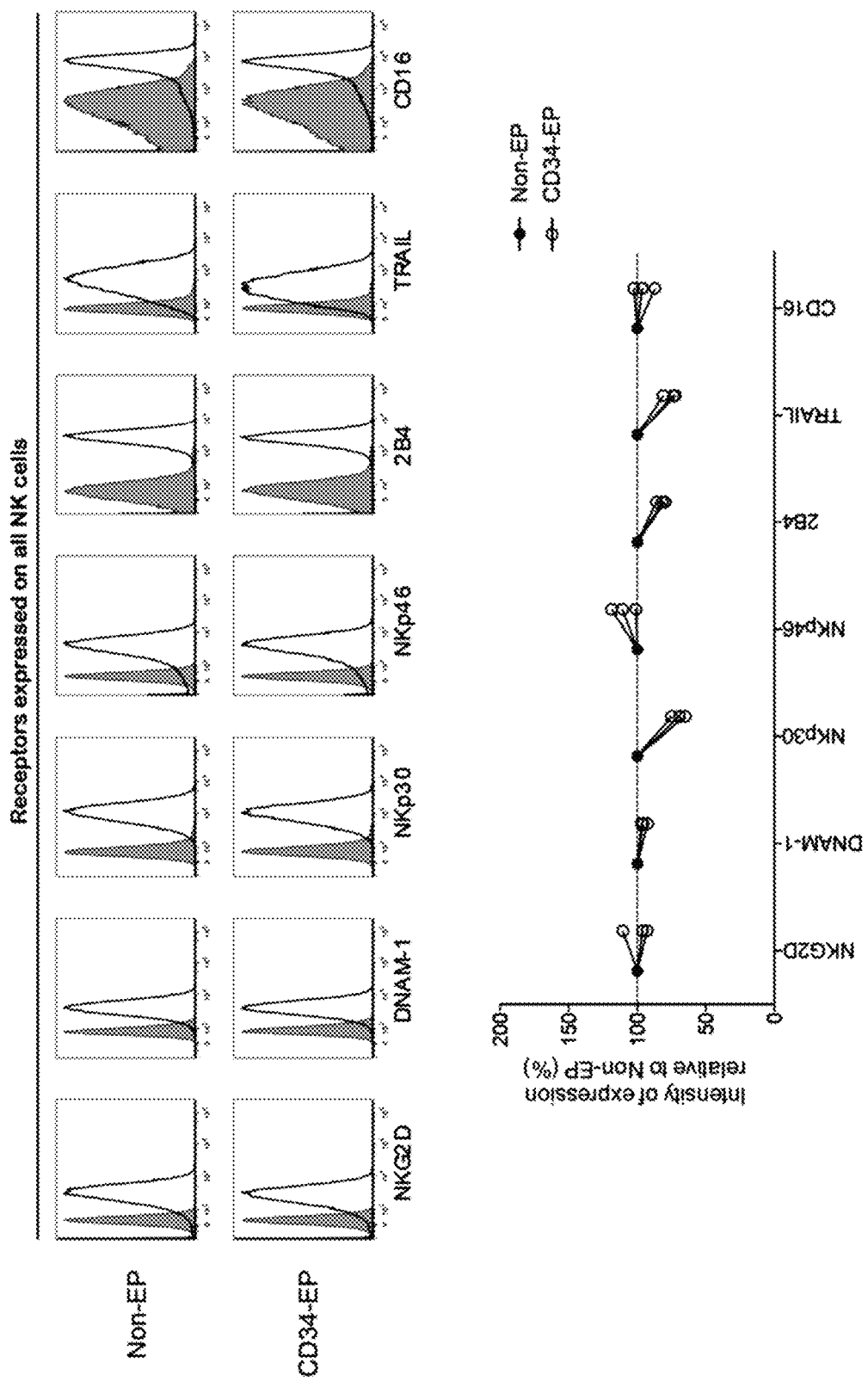

NK CELLS WITH AN INCREASED ANTIBODY-DEPENDENT CELLULAR TOXICITY (ADCC) AGAINST TUMORS

CROSS REFERENCE TO RELATED APPLICATION

This is a divisional of U.S. application Ser. No. 15/525,921, filed May 10, 2017, which is the § 371 U.S. National Stage of International Application No. PCT/US2015/060646, filed Nov. 13, 2015, which was published in English under PCT Article 21 (2), which in turn claims the benefit of U.S. Provisional Application No. 62/079,975, filed Nov. 14, 2014, which is incorporated herein by reference in its entirety.

FIELD

This disclosure relates to compositions comprising modified NK cells and their use for treating tumors or hyperproliferative disorders, for example, in combination with therapeutic anti-cancer antibodies.

SEQUENCE LISTING INCORPORATION BY REFERENCE

The Sequence Listing is submitted as an ASCII text file in the form of the file named Sequence_Listing.txt, which was created on Aug. 5, 2020, and is 24,891 bytes, which is incorporated by reference herein.

BACKGROUND

Natural killer (NK) cells are immune cells involved in the defense against cancer. They have also been shown to induce strong anti-tumor responses in the setting of hematopoietic stem cell transplantation and in early clinical trials on adoptive NK cell transfer. Several methods to expand large numbers of clinical grade NK cells have been developed for trials exploring adoptive NK cell immunotherapy for cancer. However, long-term culturing of NK cells often leads to undesirable phenotypic changes that may compromise their homing capacity and cytotoxic function, and can also lead to senescence, compromising in vivo longevity. Introducing genes into NK cells that improve their in vivo viability, cytotoxicity, and/or ability to home to disease sites could improve the efficacy of NK cell-based immunotherapy. Genetic manipulation of NK cells through viral transduction is challenging, typically resulting in substantial reduction in NK cell viability and low transduction efficiency. A need exists to for a method modify NK cells to enhance NK cell-based immunity.

SUMMARY

Disclosed herein are modified NK cells, compositions comprising modified NK cells, and methods for treating a tumor or hyperproliferative disease in a subject that include administering the modified NK cells to a subject.

In some embodiments, methods include treating a subject with a tumor, by obtaining a population of NK cells from the subject or a donor; transfecting the population of NK cells with a heterologous nucleic acid molecule encoding a CD16 protein comprising a valine at amino acid position 158, a heterologous nucleic acid molecule encoding a CCR7 protein, or both, thereby producing a population of modified NK cells, administering a composition comprising a monoclonal antibody to the subject, wherein the monoclonal antibody binds to a cell of the tumor, and administering a composition comprising the modified NK cells to the subject. In some examples, the population of NK cells are expanded in vitro prior to transfection with the nucleic acid molecule.

In some embodiments, the modified NK cells include NK cells including a heterologous nucleic acid molecule encoding a CD16 protein comprising a valine at amino acid position 158, a heterologous nucleic acid molecule encoding a CCR7 protein, or both. Also disclosed are pharmaceutical compositions including the modified NK cells. In some examples, the modified NK cells are used for treating a subject with a tumor, for example, where a subject with a tumor is pretreated with an anti-cancer monoclonal antibody followed by administration of the composition including the modified NK cells.

Some embodiments include methods of making modified NK cells. In some examples, the methods include obtaining a population of NK cells from a subject or a donor and transfecting the population of NK cells with a heterologous nucleic acid molecule encoding a CD16 protein comprising a valine at amino acid position 158, a nucleic acid molecule encoding a CCR7 protein, or both. In some examples, the NK cells are transfected with the heterologous nucleic acid(s) by electroporation. In some examples, the population of NK cells are expanded in vitro prior to transfection with the nucleic acid molecule.

In additional embodiments, the methods include treating a subject with multiple myeloma, the method including obtaining a population of natural killer (NK) cells from the subject or a donor, transfecting the population of NK cells with a nucleic acid molecule encoding a CD16 protein comprising a valine at amino acid position 158 to produce a population of modified NK cells, blocking CD38 surface antigen of the population of modified NK cells by treating with a Fab or F (ab) 2 fragment of an anti-CD38 monoclonal antibody to produce a population of CD38-blocked modified NK cells, administering a composition comprising an anti-CD38 antibody to the subject, and administering a composition comprising the population of CD38-blocked modified NK cells to the subject. In some examples, the population of NK cells are expanded in vitro prior to transfection with the nucleic acid molecule.

The foregoing and other features of the disclosure will become more apparent from the following detailed description, which proceeds with reference to the accompanying figures.

BRIEF DESCRIPTION OF THE DRAWINGS

FIG. 1A is a pair of graphs showing GFP expression (left) and viability (right, determined by Annexin V and 7-AAD from Becton Dickinson) of ex vivo expanded NK cells from healthy donors following electroporation with 0.25 µg of eGFP mRNA (TriLink Biotechnology) per million NK cells. FIG. 1B is a pair of graphs showing CD34 expression (left, determined by anti-CD34 antibody staining) and viability (right) of NK cells expanded from three healthy donors following electroporation with 1 µg of CD34 mRNA (TriLink Biotechnology) per million NK cells. FIG. 1C is a graph showing fold expansion of NK cells ex vivo following CD34 mRNA electroporation compared to non-electroporated NK cells. FIG. 1D is a series of graphs showing specific lysis of K562 cells and the multiple myeloma cell line MM1S by CD34 mRNA electroporated and non-electroporated NK cells. Non-EP, non-electroporated; GFP-EP, eGFP mRNA electroporated; CD34-EP, CD34 mRNA electroporated. A Wilcoxon ranked sum t-test was used in FIGS. 1A and 1B, whereas a paired t-test was used in FIG. 1C.

FIGS. 2A and 2B are a series of panels showing phenotypic characterization of clinical-grade ex vivo expanded NK cells following mRNA electroporation. FIG. 2A shows representative histograms for one NK cell donor (top) and pooled data from three donors (bottom) showing the relative expression intensity of selected NK cell receptors on CD34 electroporated compared to non-electroporated ex vivo expanded NK cells. FIG. 2B shows representative dot plots for one NK cell donor (top) and pooled data from three donors (bottom) showing expression of clonally expressed NK cell receptors on CD34 electroporated and non-electroporated NK cells from three healthy donors. Non-EP, non-electroporated; CD34-EP, CD34 mRNA electroporated.

FIG. 3A is a representative example of CCR7 expression on NK cells 8 hours after electroporation with CCR7 mRNA (CCR7-EP) compared to non-electroporated (Non-EP) NK cells. FIG. 3B is a graph showing correlation between CCR7 expression and CCR7 mRNA dose (Line; Linear regression). FIG. 3C is a graph showing kinetics of CCR7 expression on NK cells following electroporation with 4 µg CCR7 mRNA per million NK cells. Error bars, standard error of the mean. FIG. 3D is a graph showing transwell migration of Non-EP and CCR7-EP NK cells against a gradient of CCL19 (a ligand for CCR7). Error bars, standard error of the mean. A paired t-test was used in FIGS. 3C and 3D.

FIG. 4A is a series of graphs showing a representative example (left) and average cell surface expression (middle) of CD16 on NK cells 24 hours after electroporation with CD16 mRNA (CD16-EP) compared to non-electroporated (Non-EP) NK cells (n=7) as well as kinetics of CD16 surface expression following electroporation (right, n=3). Error bars, standard error of the mean. FIG. 4B is a series of graphs showing NK cell degranulation (measured by CD107a expression) by CD16-158V mRNA electroporated NK cells compared to Non-EP NK cells following co-culture with CD20+ 721.221 EBV-LCL cells in the absence (no mAb; no monoclonal antibody) and presence of rituximab (RTX) 24 hours after electroporation (left, n=7) as well as kinetics of NK cell ADCC following electroporation (right, n=3). Error bars, standard error of the mean. FIG. 4C is a graph showing correlation between CD16 expression and CD16-158V mRNA dose (Line; Variable slope log (agonist) vs. response regression). FIG. 4D is a graph showing correlation between NK cell CD16 expression and ADCC capacity against rituximab treated 721.221 EBV-LCL (Line; Linear regression). Wilcoxon ranked sum t-tests were used in the bar graphs in FIGS. 4A and 4B, whereas paired t-tests were used for statistics in the graphs showing kinetics of CD16 expression and NK cell ADCC.

FIG. 5A is a graph showing CD16 expression on ex vivo expanded NK cells following electroporation with mRNA encoding CD16-V158 (HA-CD16) or mRNA encoding CD34 compared to non-electroporated control NK cells. FIG. 5B is a graph showing ADCC against the MM cell line MM1S by mRNA electroporated ex vivo expanded NK cells from a donor homo-V158 electroporated; CD34-EP, CD34 electroporated.

SEQUENCE LISTING

Figure 1A:
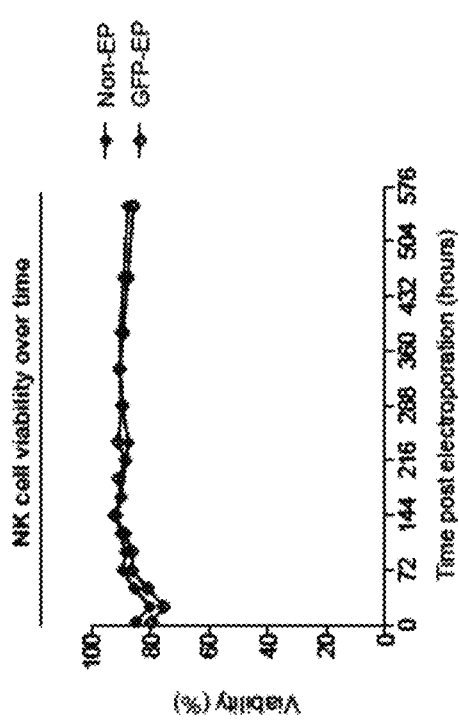
FIGS. 1A-1D are a series of panels showing transgene expression, viability, proliferative, and cytotoxic capacity of NK cells electroporated with mRNA coding for GFP or CD34 using the MAXCYTE® GT instrument.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NO: 1 is the nucleic acid sequence of an exemplary full-length CD16 nucleic acid encoding a mature protein having a phenylalanine at amino acid 158.

SEQ ID NO: 2 is the amino acid sequence of an exemplary full-length CD16 protein having a phenylalanine at amino acid position 158 of the mature protein (CD16-F158).

SEQ ID NO: 3 is the nucleic acid sequence of an exemplary full-length CD16 nucleic acid encoding a protein having a valine at amino acid 158 of the mature protein.

SEQ ID NO: 4 is the amino acid sequence of an exemplary full-length CD16 protein, which has a valine at amino acid position 158 of the mature protein (CD16-V158).

SEQ ID NO: 5 is the nucleic acid sequence of an exemplary mRNA that encodes a CD16 protein with a valine at amino acid 158 of the mature protein.

SEQ ID NO: 6 is the amino acid sequence of an exemplary CD16 protein that includes a valine at amino acid 158 of the mature protein.

SEQ ID NO: 7 is the nucleic acid sequence of an exemplary CD34 mRNA.

SEQ ID NO: 8 is the nucleic acid sequence of an exemplary full-length CCR7 nucleic acid.

SEQ ID NO: 9 is the amino acid sequence of an exemplary full-length CCR7 protein.

SEQ ID NO: 10 is the nucleic acid sequence of an exemplary full length CCR7-encoding mRNA.

DETAILED DESCRIPTION

NK cells are cytotoxic immune cells that play an important role in the defense against cancer. They have also been shown to induce anti-tumor responses in settings of hematopoietic stem cell transplantation and in pilot clinical trials utilizing adoptive NK cell transfer (Miller et al., *Blood* 105:3051-4057, 2005; Li et al., *Cancer Gene Ther.* 17:147-154, 2010). Several methods to expand clinical-grade NK cells have recently been developed that allow for multiple injections of a large number of highly cytotoxic NK cells. Preliminary data from an ongoing phase I clinical trial has established that up to $2.5 \times 10^8$ autologous ex vivo expanded NK cells/kg can be safely infused into cancer patients, with tumor regression observed in some patients (Childs et al., *Hematol. The Education Program* 2013:234-246, 2013).

Genetic manipulation of NK cells to improve their persistence, tumor targeting capacity, and/or ability to home to disease sites in vivo may further enhance the efficacy of NK cell-based cancer immunotherapy (Childs and Carlsten, *Nature Rev. Drug Discovery* 14:487-498, 2015). However, genetic manipulation of NK cells has historically proven to be challenging (Carlsten and Childs, *Front. Immunol.* 6:266, 2015). In contrast to T cells, viral transduction of NK cells induces high degrees of NK cell death and low levels of transgene expression. Due to the use of viral vectors, this approach also comes with regulatory issues, high costs and the need for specialized high-level biosafety laboratory platforms when taken to a clinical setting. Moreover, the predicted relatively short persistence of adoptively infused NK cells compared to T cells implies that stable transgene expression may not be equally necessary for this cell type.

Disclosed herein is the use of mRNA electroporation as an alternative method to genetically modify NK cells for clinical use. This approach can genetically modify cells without using viral vectors, precluding the need for high-level biosafety laboratories. Data characterizing transgene expression, viability, proliferative capacity, phenotype, and cytotoxic function of ex vivo expanded human NK cells following mRNA electroporation using a GMP-compliant platform are disclosed herein. Furthermore, disclosed herein are data demonstrating that this approach can be used to modify NK cells to improve their homing capacity to a chemokine expressed in malignant lymphoid tissues and augment their ability to mediate antibody-dependent cellular cytotoxicity (ADCC). Collectively, these data demonstrate that mRNA electroporation is an efficient method to genetically modify NK cells, with the potential to reprogram multiple NK cell properties that boost their antitumor function without incurring any major negative effects on this cellular population.

I. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." As used herein, "comprises" means "includes." Thus, "comprising A or B," means "including A, B, or A and B," without excluding additional elements. All references cited herein, including database accession numbers (such as GenBank accession numbers), are incorporated by reference as of Nov. 13, 2015.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

"Natural killer (NK) cells" are cells of the immune system that kill target cells in the absence of a specific antigenic stimulus, and without restriction according to MHC class. Target cells can be tumor cells or cells harboring viruses. NK cells are characterized by the presence of CD56 and the absence of CD3 surface markers. NK cells typically comprise approximately 10 to 15% of the mononuclear cell fraction in normal peripheral blood. Historically, NK cells were first identified by their ability to lyse certain tumor cells without prior immunization or activation. NK cells are thought to provide a "back up" protective mechanism against viruses and tumors that might escape the CTL response by down regulating MHC class I presentation. In addition to being involved in direct cytotoxic killing, NK cells also serve a role in cytokine production, which can be important to control cancer and infection.

"Activation of NK cells" refers to activation of the cytotoxic or cytostatic action of NK cells on foreign or abnormal cells or elevation of the cytotoxic or cytostatic action of pre-active (e.g., already active) NK cells on foreign or abnormal cells, as well as elevation of their other biological functions, such as stimulation of cytokine production.

"An enriched NK cell population" refers to an NK cell population selected for a sub-population of cells having a desirable anti-tumor/cytotoxic activity and are selectable by a cellular marker, e.g., a cell surface marker or intracellular marker. An enriched NK cell population can be isolated by binding a fluorescent probe to the cellular marker and selecting for the enriched NK cell population by fluorescence activated cell sorting (FACS) methods, by negative depletion using immunomagnetic beads, or other cell selection and separation technique known in the art.

"Autologous" (or "autogeneic" or "autogenous") refers to tissues, cells or DNA taken from an individual's own tissues. For example, in an autologous transfer or transplantation of NK cells, the donor and recipient are the same person. "Autologous" is related to self, or originating within an organism itself.

"Patient," "subject," or "mammal" are used interchangeably and refer to mammals such as humans and non-human primates, as well as experimental animals such as rabbits, rats, and mice, and other animals. Animals include all vertebrates, e.g., mammals and non-mammals, such as sheep, dogs, cows, chickens, amphibians, and reptiles.

"Treating" or "treatment" includes the administration of one or more compositions, compounds, or agents (such as a population of modified NK cells) to prevent or delay the onset of symptoms, complications, and/or biochemical indicia of a disease; alleviating the symptoms; or arresting or inhibiting further development of the disease, condition, or disorder (e.g., cancer, metastatic cancer, metastatic solid tumors, or hyperproliferative disease). Treatment can be prophylactic (e.g., adjuvant, to prevent or delay the onset of the disease, or to prevent the manifestation of clinical or subclinical symptoms thereof) or therapeutic (e.g., suppression or alleviation of symptoms after the manifestation of the disease).

"An amount effective to reduce or eliminate the tumor or to prevent its occurrence or recurrence" or "an amount effective to reduce or eliminate the hyperproliferative disorder or to prevent its occurrence or recurrence" refers to an amount of a compound, composition, or agent that improves a patient outcome or survival following treatment for the tumor disease state or hyperproliferative disorder as measured by patient test data, survival data, elevation or suppression of tumor marker levels, reduced susceptibility based upon genetic profile, or exposure to environmental factors.

"Cancer" is used synonymously to the terms "tumor," "malignant tumor," "malignant neoplasm," or "hyperproliferative disorder" and refers to any of a number of diseases that are characterized by uncontrolled, abnormal proliferation of cells, the potential of cancer cells to spread locally or through the bloodstream and lymphatic system to other parts of the body (e.g., metastasize), as well as any of a number of characteristic structural and/or molecular features. A "cancer cell" is a cell having specific structural properties, lacking differentiation and being capable of invasion and metastasis. "Cancer" as used herein includes all types of cancers found in mammals, including carcinomas, sarcomas, and tumors of the hematopoietic or lymphoid tissues. Non-limiting examples include cancers of the breast, lung, non-small cell lung, stomach, brain, head and neck, medulloblastoma, bone, liver, colon, genitourinary, bladder, urinary, kidney, testes, uterus, ovary, cervix, prostate, melanoma, mesothelioma, sarcoma, leukemias, and lymphomas (see DeVita, et al., (eds.), 2001, *Cancer Principles and Practice of Oncology*, 6th. Ed., Lippincott Williams & Wilkins, Philadelphia, PA; this reference is herein incorporated by reference in its entirety for all purposes).

"Cancer-associated" refers to the relationship of a nucleic acid and its expression, or lack thereof, or a protein and its level or activity, or lack thereof, to the onset of malignancy in a subject cell. For example, cancer can be associated with expression of a particular gene that is not expressed, or is expressed at a lower level, in a normal healthy cell. Conversely, a cancer-associated gene can be one that is not expressed in a malignant cell (or in a cell undergoing transformation), or is expressed at a lower level in the malignant cell than it is expressed in a normal healthy cell.

In the context of the cancer, the term "transformation" refers to the change that a normal cell undergoes as it becomes malignant. In eukaryotes, the term "transformation" can be used to describe the conversion of normal cells to malignant cells in cell culture.

"Hyperproliferative disease" refers to any disease or disorder in which the cells proliferate more rapidly than normal tissue growth. Thus, a hyperproliferating cell is a cell that is proliferating more rapidly than normal cells.

"Melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

"CD16" (also known as FcγRIII) is a receptor for the Fc portion of IgG. It is expressed on NK cells and is involved in antibody-dependent responses (such as NK cell-mediated ADCC). There are two CD16 genes in humans-CD16a (FcγRIIIa) and CD16b (FcγRIIIb). As used herein, "CD16" refers to CD16a and is used interchangeably with CD16a or FcγRIIIa. The majority of humans express CD16 which has a relatively low affinity for IgG1 antibodies. However, a single nucleotide polymorphism (SNP rs396991) in the CD16 gene, resulting in an amino acid substitution of valine (V) for phenylalanine (F) at position 158 (F158V) in the mature (processed) form of the protein, is associated with substantially higher affinity for IgG1 antibodies and superior NK cell-mediated ADCC. The higher affinity variant is referred to herein as HA-CD16 or CD16-V158; the lower affinity variant is referred to as LA-CD16 or CD16-F158.

Nucleic acid and protein sequences for CD16a are publicly available. For example, GenBank Accession Nos. NM_000569 (SEQ ID NO: 1), NM_001127596, NM_001127595, NM_001127593, and NM_001127592 disclose exemplary human CD16a nucleic acid sequences, and GenBank Accession Nos. NP_000560 (SEQ ID NO: 2), NP_001121068, NP_001121067, NP_00112065, and NP_001121064 disclose exemplary human CD16a protein sequences. One of ordinary skill in the art can identify additional CD16a nucleic acid and amino acid sequences that vary from those provided herein, but that retain at least one activity of CD16a, such as Fc binding activity.

"CCR7" is a chemokine receptor (chemokine (C-C motif) receptor 7), which is known to direct cellular migration to secondary lymphoid tissues, including lymph nodes where hematological malignancies such as lymphoma reside. The CCR7 receptor is normally expressed by only a small subset of resting primary NK cells (primarily the CD56$^{bright}$ NK cell subset).

Nucleic acid and protein sequences for CCR7 are publicly available. For example, GenBank Accession Nos. NM_001301714, NM_001838 (SEQ ID NO: 8), NM_001301717, NM_001301716, and NM_001301718 disclose exemplary human CCR7 nucleic acid sequences, and GenBank Accession Nos. NP_001288643, NP_001829 (SEQ ID NO: 9), NP_001288646, NP_001288645, and NP_001288647 disclose exemplary human CCR7 protein sequences. One of ordinary skill in the art can identify additional CCR7 nucleic acid and amino acid sequences that vary from those provided herein, but that retain at least one activity of CCR7, such as binding of and/or cellular migration toward CCR7 ligands such as CCL19 and CCL21.

"Antibody-dependent cell-mediated cytotoxicity (ADCC)" is a process that can kill sensitive targets, including tumor cells and virally infected cells, in which NK cells are the effectors. ADCC is triggered when receptors on the NK cell surface (such as CD16) recognize IgG1 or IgG3 antibodies bound to the surface of a cell. This triggers release of cytoplasmic granules containing perforin and granzymes, leading to target cell death.

"Transduce" or "transfect" refers to transfer of nucleic acid into a cell, such as transfer of a heterologous nucleic acid into a host cell. As used herein, these terms include all techniques by which a nucleic acid is introduced into a cell, including but not limited to transformation with plasmid vectors, infection with viral vectors, and introduction of naked DNA by electroporation, nucleofection, lipofection, or particle gun acceleration.

A "heterologous" nucleic acid refers to a nucleic acid originating from a different genetic source. For example, a nucleic acid that is heterologous to a cell originates from an organism or individual other than the cell in which it is expressed.

II. Modified NK Cells

Disclosed herein are modified NK cells, such as NK cells expressing a heterologous CD16-V158 encoding nucleic acid, a heterologous CCR7 encoding nucleic acid, or a combination thereof. Also disclosed are methods of preparing the modified NK cells. The methods include transfecting or transducing NK cells (such as ex vivo expanded or enriched NK cells) with one or more heterologous nucleic acids to express CD16 (for example, CD16-V158), CCR7, or both. In some examples, the heterologous nucleic acid(s) is transiently maintained in the cell into which it is introduced, for example, it is present in the modified cell as an episomal or extrachromosomal nucleic acid. In other examples, the heterologous nucleic acid(s) is stably maintained in the cell, for example, by integration into the genome of the cell.

Methods of eukaryotic cell transfection and prokaryotic cell transformation are known to one of ordinary in the art. Methods of transfection include calcium phosphate (Chen et al., 1988, Calcium phosphate-mediated gene transfer: A highly efficient system for stably transforming cells with plasmid DNA *BioTechniques* 6:632-38), DEAE-dextran (Fujita et al., 1986, Regulation of human interleukin-2 gene: Functional DNA sequences in the 5' flanking region for the gene expression in activated T lymphocytes, *Cell* 46:401-07), cationic lipids (Elroy-Stein, et al., 1990, Cytoplasmic expression system based on constitutive synthesis of bacteriophage T7 RNA polymerase in mammalian cells, *Proc. Natl. Acad. Sci. USA* 87:6743-47), retrovirus (Miller, et al., 1986. Redesign of retrovirus packaging cell lines to avoid recombination leading to helper virus production, *Mol. Cell. Biol.* 6:2895-902), polybrene (Chaney, et al., 1986, High-frequency transfection of CHO cells using Polybrene, *Somatic Cell Mol. Genet.* 12:237), microinjection (Capecchi, 1980, High efficiency transformation by direct microinjection of DNA into cultured mammalian cells, *Cell* 22:479), and electroporation (Neumann et al., 1982, Gene transfer into mouse lyoma cells by electroporation in high electric fields, *EMBO J.* 1:841-45). NK cells may also be genetically modified by viral transduction, including using retroviral vectors, lentiviral vectors, adenoviral vectors, or vaccinia virus vectors.

Transfection (e.g., electroporation, nucleofection, or lipofection methods) of NK cells produces high transduction efficiency and maintains the viability of the cells. In addition, these methods do not rely on viral vectors, and so, face fewer regulatory hurdles and do not require high level biosafety laboratory production. Transfection produces only transient expression of the nucleic acid introduced into the cell (e.g., for about 6-96 hours), unlike viral transduction, which produces stable transgene expression. However, in the methods disclosed herein, it is expected that the desired ADCC activity of the NK cells will occur relatively quickly following administration of the modified NK cells and a mAb. Thus, transient expression of the introduced nucleic acid (such as CD16, CCR7, or both) may be sufficient to achieve the desired therapeutic effect. Furthermore, viral transduction methods carry risk of insertional mutagenesis and immunogenicity, as well as possible off tumor toxicity (for example, dysregulated immunity with CD16-V158 expression). Transient transfection methods avoid these risks, although modifications to viral vectors and transduction methods may mitigate these risks.

In some examples, described herein, NK cells are electroporated with a nucleic acids encoding CD16, CCR7, or both. Electroporation is a method that utilizes a short electric pulse that temporarily induces the formation of small pores in the cell membrane, allowing charged molecules (such as nucleic acid molecules) to enter the cell. Utilizing mRNA (rather than cDNA), transfection efficiencies of 80-90% or more can be achieved with resting or expanded NK cell populations.

A. Isolation and Enrichment of NK Cells

Techniques for the in vitro isolation and large-scale expansion of NK cells is described herein. An exemplary procedure is described in US Pat. App. Publ. No. 2014/0086890, incorporated herein by reference in its entirety. One of ordinary skill in the art can identify additional methods for expanding NK cells, for example as described in Childs et al., *Hematol. The Education Program* 2013: 234-246, 2013, incorporated herein by reference in its entirety.

Mononuclear cells are collected from a subject (such as a donor subject or a subject with a tumor or hyperproliferative disease). In some examples, mononuclear cells are collected by an apheresis procedure. The mononuclear cells are enriched for NK cells, for example by negative depletion using an immuno-magnetic bead strategy. In some examples, NK cells are enriched by depleting the mononuclear cell sample of T cells, B cells, monocytes, dendritic cells, platelets, macrophages, and erythrocytes utilizing a mixture of biotinylated monoclonal antibodies. The non-NK cells in the sample are removed with magnetic beads coupled to streptavidin, resulting in an enriched preparation of NK cells. An exemplary commercially available kit for this method is Dynabeads® Untouched™ Human NK Cells kit (Thermo Fisher Scientific, Waltham, MA). In another example, NK cells are enriched by positive selection of $CD56^+$ NK cells, for example utilizing magnetic beads conjugated to an anti-CD56 antibody (such as CD56 Micro-Beads, Miltenyi Biotec, Inc., Auburn, CA). In other examples, a two-step method including negative depletion (such as T cell depletion) followed by positive selection of CD56+NK cells is used for enriching NK cells. These methods can be carried out under or adapted for Current Good Manufacturing Practice (cGMP). One of ordinary skill in the art can identify other methods that can be used to prepare an enriched population of NK cells.

Enriched NK cells (typically >99% CD3 negative and >85% CD56+) are expanded in vitro. In one non-limiting example, the enriched NK cells are cultured with an irradiated EBV-LCL feeder cell line (SMI-LCL) in X-VIVO™ 20 medium (Lonza, Basel, Switzerland) with 10% human AB serum and 500 IU/ml of interleukin-2 (IL-2), for up to 21 days. Utilizing this technique, expansions of NK cells in the range of 200- to 1000-fold may be achieved (expanded NK cells are typically >99% CD3 negative and >90% CD56+). In some examples, the starting population of enriched NK cells is about $0.8\text{-}1.6\times10^8$ total NK cells, which over a 2-4 week period expand up to 1000-fold or greater in vitro. Similar numbers of NK cells have been expanded in scaled up experiments using GMP conditions. In some examples, NK cells are expanded in G-Rex® containers (Wilson Wolf, New Brighton, MN). The G-Rex®100 container support NK expansions to doses of $2.5\times10^8$ NK cells/kg or higher. NK cells cultured in G-Rex® 100 containers could be cultured at concentrations up to $4\times10^6$ NK cells/ml.

Bulk NK cells or NK cells subsets isolated by additional enriching procedures, such as through the use of immune-magnetic beads or flow sorting, may be grown in cell culture medium, e.g., Cellgro SCGM scrum-free media (CellGenix, Gaithersburg, MD) containing 10% human AB serum, 50 U/mL penicillin, 50 μg/mL streptomycin, and 500 IU/mL IL-2 or in X-VIVO™ 20 media containing 10% heat inactivated human AB serum or 10% autologous serum.

Non-expanded and expanded NK cells can be analyzed by flow cytometry for the expression of markers such as CD56, CD16, TRAIL, FasL, NKG2D, LFA-1, perforin, and granzymes A and B. In some examples, expression of one or more of the markers is measured at baseline and ≥10 days following in vitro expansion. Chromium release assays can be used to assess fresh vs. expanded NK cell cytotoxicity against cancer cell targets. One of ordinary skill in the art can identify other methods to assess the NK cell population (for example, purity), viability, and/or activity.

In vitro-expanded NK cells are phenotypically and functionally different from non-expanded NK cells. Freshly-isolated (resting) NK cells do not express TRAIL or FasL; in contrast, NKG2D, LFA-1, perforin and granzymes A and B are constitutively expressed in resting NK cells. Expanded cells have increased NKG2D and TRAIL expression and greatly enhanced TRAIL-mediated tumor cytotoxicity compared to non-expanded NK cells. Furthermore, expanded NK cells down-regulate CD16 expression.

B. Modified NK Cells Expressing CD16

Antibody-based therapies can benefit from the presence of NK cells having known high levels of Fc-binding capacity and cytotoxic activity within the subject. Further, NK cells isolated from cancer subjects are often found to have been rendered defective, deficient, or ineffective by actions of the tumor cells. Other types of tumor cells similarly are able to interfere with NK cell production, activity, and/or specificity. Such variability makes reliance on subject NK cells problematic in a therapeutic setting and suggests that the co-administration of known quantities of exogenous NK cells having a known level of activity, along with an appropriate antibody, can result in more consistent therapeutic effects. The availability of a clonal human NK cell population that expresses a consistent level of CD16 activity is expected to provide substantial benefit.

CD16 is a cluster of differentiation molecule found on the surface of natural killer cells, neutrophil polymorphonuclear leukocytes, monocytes and macrophages. It can be used to isolate populations of these cells by antibodies directed towards CD16, using fluorescent-activated cell sorting or magnetic-activated cell sorting. CD16 has been identified as Fc receptors, including FcγRIIIa (CD16a) and FcγRIIIb (CD16b). These receptors bind to the Fc portion of IgG antibodies (such as IgG1), which then activates the NK cell for antibody-dependent cell-mediated cytotoxicity. A lack of CD16 in a given population of neutrophils may indicate prematurity, as could be caused by a left-shift due to neutrophilic leukocytosis induced by tissue necrosis or bacterial infection.

CD16 affinity for the Fc component of monoclonal antibodies is an important determinant for response to mAb antibody therapy for patients with cancers, including cancers such as lymphoma and breast cancer. Unfortunately, about 90% of patients receiving mAb therapy for cancer only express the low affinity CD16 receptor (CD16-F158), which decreases the ability of NK cells to mediate ADCC. Transfection or transduction of NK cells (for example, by electroporation) with a nucleic acid coding for the high affinity CD16 receptor variant (CD16-V158) may improve the outcome in patients treated with any anti-tumor targeting antibody where such an antibody mediates tumor cytotoxicity at least in part by ADCC. With this approach, it is possible to infuse a large number of highly cytotoxic autologous ex vivo expanded NK cells expressing CD16-V158 into cancer patients receiving treatment with any FDA approved mAb to induce an increased anti-tumor response than would occur with treatment of the mAb alone. This therapy has applicability to bolster anti-tumor responses in patients receiving anti-cancer antibody treatment, as described in detail herein.

FcγRIIIa is also known as FCGR3A, CD16, CD16A, FCG3, FCGR3, FCGRIII, FCR-10, FCRIII, FCRIIIA, IGFR3, and IMD20. The FcγRIIIa mRNA encodes a receptor for the Fc portion of immunoglobulin G, and it is involved in the removal of antigen-antibody complexes from the circulation, as well as other antibody-dependent responses. This gene (FCGR3A) is highly similar to another nearby gene (FCGR3B) located on chromosome 1. The receptor encoded by FCGR3A is expressed on NK cells as an integral membrane glycoprotein anchored through transmembrane peptide, whereas FCGR3B is expressed on polymorphonuclear neutrophils, where the receptor is anchored through a phosphatidylinositol linkage. Mutations in this gene have been linked to susceptibility to recurrent viral infections, susceptibility to systemic lupus erythematosus, and alloimmune neonatal neutropenia.

The majority of humans express CD16 which has a relatively low affinity for IgG1 antibodies. However, a single nucleotide polymorphism (SNP rs396991) in the CD16 gene, resulting in an amino acid substitution at position 158 (F158V), is associated with substantially higher affinity for IgG1 antibodies and superior NK cell-mediated ADCC than those with the 158F genotype. The high-affinity CD16-V158 polymorphism (also referred to as HA-CD16) has also been linked to enhanced ADCC capacity in vivo, as exemplified by studies in which lymphoma patients homozygous for CD16-V158 showed more durable disease regression following treatment with the anti-CD20 antibody rituximab compared to those lacking homozygosity for CD16-V158 (CD16-158F/F or V/F).

An exemplary sequence of FcγRIIIa (CD16) mRNA is NM_000569 (SEQ ID NO: 1). The CD16 mRNA sequence encodes a protein that includes a signal peptide, coded by nucleotides 185-343 of SEQ ID NO: 1 or SEQ ID NO: 3. The processed (mature) CD16 protein is encoded by nucleotides 344-1054 of SEQ ID NO: 1 or SEQ ID NO: 3. SEQ ID NO: 2 (encoded by SEQ ID NO: 1) and SEQ ID NO: 4 (encoded by SEQ ID NO: 3) each include a fifty-three amino acid signal peptide. The signal peptide (amino acids 1-53 of SEQ ID NO: 2 or SEQ ID NO: 4) is cleaved from the protein to produce the mature form of the protein. The mature protein encoded by SEQ ID NO: 1 has a phenylalanine at amino acid 158 (corresponding to amino acid 212 of SEQ ID NO: 2), encoded by the TTT trinucleotide at nucleotide positions 818-820 of SEQ ID NO: 1. Substituting a G at nucleotide 818 of SEQ ID NO: 1 results in a GTT trinucleotide encoding a valine at amino acid 158 of the mature CD16 protein (corresponding to amino acid 212 of SEQ ID NO: 4). This is shown in the sequence NM_000569/T818G (SEQ ID NO: 3).

SEQ ID NO: 5 is an exemplary mRNA sequence encoding a CD16 protein. SEQ ID NO: 5 encodes a CD16 protein including a 17 amino acid signal peptide (nucleotides 1-51 of SEQ ID NO: 5, encoding amino acids 1-17 of SEQ ID NO: 6). This mRNA encodes a CD16 protein that has a valine at amino acid position 158 of the mature (processed) form of the protein (corresponding to amino acid 176 of SEQ ID NO: 6).

Thus, in particular examples, the modified NK cells disclosed herein are NK cells (such as a population of enriched or expanded NK cells) that include a heterologous nucleic acid encoding CD16-V158, such as NK cells that include a nucleic acid having the sequence of SEQ ID NO: 3 or SEQ ID NO: 5. In particular examples, the modified NK cells express a CD16-V158 protein, such as SEQ ID NO: 4 or SEQ ID NO: 6.

In some examples, the transfected or transduced nucleic acid is in the form of mRNA, or RNA or DNA encoding CD16 mRNA. The transfected RNA or DNA can include a viral or plasmid vector. In particular examples, a population of expanded NK cells is electroporated with a nucleic acid (such as an RNA or mRNA) encoding a CD16-V158 protein. In one non-limiting example, NK cells (such as enriched or expanded NK cells) are electroporated with an RNA having the nucleotide sequence of SEQ ID NO: 3 or SEQ ID NO: 5.

Methods of electroporating cells, including NK cells are known in the art. In some examples, the modified NK cells disclosed herein are produced using a MAXCYTE® Transfection System with conditions optimized for transfection of NK cells. In one non-limiting example, NK cells are electroporated as described in Example 1.

In additional examples, the modified NK cells include a nucleic acid encoding an alternatively spliced variant of CD16 (such as GenBank Accession Nos. NM_001127596, NM_001127595, NM_001127593, and NM_001127592) that also encode (or are modified to encode) a valine at amino acid position 158. In further examples, the modified NK cells include a nucleic acid having at least 90% sequence identity (such as at least 91%, 92%, 93%, 94%, 95%, 96%, 97%, 98%, 99%, or more identity) with SEQ ID NO: 3, SEQ ID NO: 5, or GenBank Accession Nos. NM_001127596, NM_001127595, NM_001127593, or NM_001127592 (e.g., modified to encode a valine at amino acid position 158). Thus in some examples, expanded NK cells are transfected with a nucleic acid having at least 90% sequence identity (such as at least 91%, 92%, 93%, 94%, 95%, 96%, 97%, 98%, 99%, or more identity) with SEQ ID NO: 3, SEQ ID NO: 5, or GenBank Accession Nos. NM_001127596, NM_001127595, NM_001127593, or NM_001127592 (modified to encode a valine at amino acid position 158). The resulting modified NK cells express a protein having at least 90% sequence identity (such as at least 91%, 92%, 93%, 94%, 95%, 96%, 97%, 98%, 99%, or more identity) with SEQ ID NO: 4, SEQ ID NO: 6, or GenBank Accession Nos. NP_001121068, NP_001121067, NP_00112065, and NP_001121064 (having a valine at amino acid position 158).

Following transfection of NK cells, the expression of CD16-V158 can be determined by methods known to one of ordinary skill in the art, such as flow cytometry using a labeled anti-CD16 antibody. In some examples, the methods described herein produce a population of NK cells in which at least 80% of the cells express detectable amounts of CD16-V158 within 24-72 hours of transfection (for example, electroporation). In particular examples, at least 80%, 85%, 90%, 95%, 98%, 99% or more of the transfected NK cells express detectable amounts of CD16-V158 24 hours after transfection. In other examples, the transfected expanded NK cells express about 2-fold to 3-fold more CD16 than control (non-transfected) expanded NK cells within about 8-48 hours of transfection. In some examples, transfection (e.g., electroporation) of the expanded NK cells does not decrease (for example, does not statistically significantly decrease) proliferation, viability or cytotoxicity against tumor cells compared to control (non-transfected) expanded NK cells.

C. Modified NK Cells Expressing CCR7

Disclosed herein are modified NK cells overexpressing CCR7. Overexpression of CCR7 in NK cells to increase homing of adoptively infused NK cells to lymphoid tissues is a treatment strategy in patients with lymphoma as well as in patients who have tumors that have metastasized to lymphoid tissues. NK cells can also be modified to overexpress other chemokine receptors to increase targeting of adoptively infused NK cells to sites of tumor cells. Thus, although modified NK cells overexpressing CCR7 are described herein, similar methods can be utilized to prepare modified NK cells overexpressing one or more additional chemokine receptors or other molecules, including, but not limited to CXCR4, VLA-4 (e.g., ITG4A, ITGB1, or both), and/or LFA-1 (e.g., ITGB2, ITGAL, or both), for example, to increase targeting of the modified NK cells to bone marrow. One of ordinary skill in the art can identify other chemokine receptors or other molecules for expression in modified NK cells (alone or in combination with expression of CD16).

CCR7 encodes a protein that is a member of the G protein-coupled receptor family. It was originally identified as being induced by Epstein Barr virus, and is a potential mediator of EBV effects on B lymphocytes. CCR7 is expressed in lymphoid tissues and activates B and T lymphocytes. The chemokine (CC-motif) ligands CCL19 and CCL21 are ligands for CCR7. The activities of CCR7 include regulating migration of cells to lymphoid organs, such as homing of naïve and regulatory T cells to lymph nodes and inflammation-induced migration of dendritic cells to lymph nodes. The CCR7 receptor is normally expressed by only a small subset of resting primary NK cells (primarily the CD56$^{bright}$ NK cell subset) and is not normally expressed in expanded NK cells.

A reference sequence of the CCR7 is SEQ ID NO: 8, which encodes the protein having the amino acid sequence of SEQ ID NO: 9. SEQ ID NO: 8 encodes a signal peptide (nucleotides 1-72 of SEQ ID NO: 8, corresponding to amino acids 1-24 of SEQ ID NO: 9). The signal sequence is cleaved from the CCR7 protein to produce the mature CCR7 protein (corresponding to amino acids 25-378 of SEQ ID NO: 9). An exemplary CCR7 mRNA sequence is disclosed herein as SEQ ID NO: 10, which encodes the protein of SEQ ID NO: 9. SEQ ID NO: 10 also includes the signal sequence (nucleotides 1-72 of SEQ ID NO: 10).

Thus, in particular examples, the modified NK cells disclosed herein are NK cells (such as a population of enriched or expanded NK cells) that include an exogenous nucleic acid encoding CCR7, such as NK cells that include a nucleic acid having the sequence of SEQ ID NO: 8 or SEQ ID NO: 10. In particular examples, the modified NK cells express a CCR7 protein, such as SEQ ID NO: 9.

In some examples, the transfected or transduced nucleic acid is in the form of mRNA, or RNA or DNA encoding CCR7 mRNA. The transfected RNA or DNA can include a viral or plasmid vector. In particular examples, a population of expanded NK cells is transfected (e.g., electroporated) with a nucleic acid (such as an RNA or mRNA) encoding a CCR7 protein. In one non-limiting example, NK cells (such as enriched or expanded NK cells) are electroporated with an RNA having the nucleotide sequence of SEQ ID NO: 10. Methods of electroporating cells, including NK cells are known in the art. In some examples, the modified NK cells disclosed herein are produced using a MAXCYTE® Transfection System with conditions optimized for transfection of NK cells, as discussed above.

In additional examples, the modified NK cells include a nucleic acid encoding an alternatively spliced variant of CCR7 (such as GenBank Accession Nos. NM_001301714, NM_001838, NM_001301717, NM_001301716, and NM_001301718). In further examples, the modified NK cells include a nucleic acid having at least 90% sequence identity (such as at least 91%, 92%, 93%, 94%, 95%, 96%, 97%, 98%, 99%, or more identity) with SEQ ID NO: 8 or 10 or GenBank Accession Nos. NM_001301714, NM_001838, NM_001301717, NM_001301716, and NM_001301718. Thus in some examples, expanded NK cells are transfected with a nucleic acid having at least 90% sequence identity (such as at least 91%, 92%, 93%, 94%, 95%, 96%, 97%, 98%, 99%, or more identity) with SEQ ID NO: 8, SEQ ID NO: 10, or GenBank Accession Nos. NM_001301714, NM_001838, NM_001301717, NM_001301716, or NM_001301718. The resulting modified NK cells express a protein having at least 90% sequence identity (such as at least 91%, 92%, 93%, 94%, 95%, 96%, 97%, 98%, 99%, or more identity) with SEQ ID NO: 9 or GenBank Accession Nos. NP_001288643, NP_001829, NP_001288646, NP_001288645, and NP_001288647.

Following transfection, the expression of CCR7 can be determined by methods known to one of ordinary skill in the art, such as flow cytometry using a labeled anti-CCR7 antibody. In some examples, the methods described herein produce a population of NK cells in which at least 80% of the cells express detectable amounts of CCR7 within 24-72 hours of transfection. In particular examples, at least 80%, 85%, 90%, 95%, 98%, 99% or more of the transfected (e.g., electroporated) NK cells express detectable amounts of CCR7 24 hours after electroporation. In other examples, the transfected expanded NK cells express about 2-fold to 3-fold more CCR7 than control (non-transfected) expanded NK cells within about 8-24 hours of electroporation. In further examples, the transfected expanded NK cells exhibit increased migration toward CCL19 or CCL21 (for example statistically significantly increased migration) compared to non-transfected expanded NK cells, such as about 2-4-fold increased migration. In some examples, transfection of the expanded NK cells does not decrease (for example, does not statistically significantly decrease) proliferation, viability or cytotoxicity against tumor cells compared to control (non-transfected) expanded NK cells.

D. Modified NK Cells Expressing CD16 and CCR7

Also disclosed herein are modified NK cells that include a heterologous CD16 nucleic acid (such as a CD16-V158 protein-encoding nucleic acid) and a heterologous CCR7 nucleic acid (such as a CCR7 protein-encoding nucleic acid). In some embodiments, the modified NK cells, which overexpress CD16-V158 and CCR7 are advantageous to both increase ADCC activity of NK cells against a tumor and to target the NK cells to the site of a tumor in lymphoid tissue (such as a lymphoma) or a metastasis to lymphoid tissue.

Thus, in particular examples, the modified NK cells disclosed herein are NK cells (such as a population of enriched or expanded NK cells) that include a heterologous nucleic acid encoding CD16-V158 and a nucleic acid encoding CCR7, such as NK cells that include a nucleic acid having the sequence of SEQ ID NO: 3 or SEQ ID NO: 5 and a nucleic acid having the sequence of SEQ ID NO: 8 or SEQ ID NO: 10. In particular examples, the modified NK cells express a CD16-V158 protein, such as SEQ ID NO: 4 or SEQ ID NO: 6 and a CCR7 protein, such as SEQ ID NO: 9.

In some examples, the transfected or transduced nucleic acids are in the form of mRNA, RNA or DNA encoding CD-V158 and mRNA, RNA or DNA encoding CCR7. The transfected RNA or DNA can include a viral or plasmid vector. In particular examples, a population of expanded NK cells is electroporated with two nucleic acids (such as an RNA or mRNA), one encoding a CD16-V158 protein and one encoding a CCR7 protein. In some examples, the CD16-V158 nucleic acids (and encoded proteins) and CCR7 nucleic acids (and encoded proteins) include any of the nucleic acid and protein sequences described herein. In one non-limiting example, NK cells (such as enriched or expanded NK cells) are electroporated with an RNA having the nucleotide sequence of SEQ ID NO: 5 and an RNA having the nucleotide sequence of SEQ ID NO: 10.

Methods of electroporating cells, including NK cells are known in the art. In some examples, the modified NK cells disclosed herein are produced using a MAXCYTE® Transfection System with conditions optimized for transfection of NK cells, as discussed above. The electroporation protocol may be modified to accommodate transfection of two (or more) nucleic acids. For example, the NK cells may be electroporated with an increased amount of total mRNA compared to electroporation of a single mRNA, in order to maintain a high (e.g., >80%) transfection efficiency. One of ordinary skill in the art can optimize the concentrations of mRNA used for electroporation using routine methods, for example as described in Examples 3 and 4.

As discussed above, NK cells overexpressing chemokine receptors other than CCR7 or other cell surface molecules (such as CXCR4, VLA-4, and/or LFA-1) can also be prepared, for example to increase targeting of adoptively infused NK cells to sites of tumor cells. Thus, the methods described herein can be used to prepare modified NK cells co-expressing CD16-V158 and any chemokine receptor or other molecule of interest.

III. Anti-Cancer Monoclonal Antibodies

The modified NK cells described herein are useful in enhancing therapeutic responses to anti-cancer monoclonal antibodies (mAbs). Table 1 lists exemplary mAbs currently in clinical studies or being marketed as FDA-approved biological therapeutics that can be utilized with the modified NK cells to treat a subject with a tumor or hyperproliferative disease.

TABLE 1

Exemplary therapeutic monoclonal antibodies

| Antigen | mAb<br>murine: -tumomab;<br>chimeric: -tuximab;<br>humanized: -tuzumab<br>human: -tumumab | Target Tumor/Disease |
|---|---|---|
| CD19 | GBR 401, MEDI-551 | B cell lymphoma, CLL |
| CD20 | Rituximab (RITUXAN ®), ofatumumab (ARZERRA ®), and veltuzumab | Non-Hodgkin's lymphoma |
|  | Ibritumomab tiuxetan (ZEVALIN ®), obinutuzumab, ublituximab, tositumomab (BEXXAR ®), ocaratuzumab | Lymphoma |
| CD22 | Namatumab, inotuzumab ozogamicin | Cancer |

TABLE 1-continued

Exemplary therapeutic monoclonal antibodies

| Antigen | mAb<br>murine: -tumomab;<br>chimeric: -tuximab;<br>humanized: -tuzumab<br>human: -tumumab | Target Tumor/Disease |
| --- | --- | --- |
| CD30 | Brentuximab vedotin (ADCETRIS ®), iratumumab | Hodgkin's lymphoma |
| CD33 | Gemtuzumab ozogamicin (MYLOTARG ®), lintuzumab, | Acute myelogenous leukemia |
| CD37 | Otlertuzumab | Cancer cells |
| CD38 | Daratumumab | Multiple myeloma |
| CD40 | Lucatumumab, dacetuzumab | multiple myeloma, non-Hodgkin's or Hodgkin's lymphoma |
| CD52 | Alemtuzumab (CAMPATH ®, MABCAMPATH ® and CAMPATH-1H ®) | Chronic lymphocytic leukemia |
| CD56 | Lorvotuzumab mertansine | small-cell lung cancer, ovarian cancer |
| CD70 | Vorsetuzumab mafodotin | Renal cell carcinoma |
| CD74 | Milatuzumab | Multiple myeloma |
| CD140 | Tovetumab | cancer |
| EpCAM | IGN101, oportuzumab monatox, tucotuzumab celmoleukin, and adecatumumab | Epithelial tumors (breast, colon and lung) |
| CEA | Labetuzumab (CEA-CIDE ®) | Breast, colon and lung tumors |
| gpA33 | huA33 | Colorectal carcinoma |
| mesothelin | Amatuximab | Cancer cells |
| α-fetoprotein | $^{90}$Y-tacatuzumab tetraxetan | Tumor cells |
| IL-6 | Siltuximab | metastatic renal cell cancer, prostate cancer, and Castleman's disease |
| Mucins | Pemtumomab (THERAGYN ®), cantuzumab mertansine, $^{90}$Y clivatuzumab tetraxetanand, oregovomab (OVAREX ®) | Breast, colon, lung and ovarian tumors |
| PDGFR-alpha | Olaratumab | Solid tumors |
| TAG-72 | CC49 (minretumomab) | Breast, colon and lung tumors |
| CAIX | Girentuximab, cG250 | Renal cell carcinoma |
| PSMA | J591 | Prostate carcinoma |
| Folate-binding protein | MOv18 and MORAb-003 (farletuzumab) | Ovarian tumors |
| Scatter factor receptor kinase | Onartuzumab | Cancer cells |
| Gangliosides (e.g, GD2, GD3 and GM2) | 3F8, ch14.18 and KW-2871 | Neuroectodermal tumors and some epithelial tumors |
| Cytokeratin | $^{99m}$Tc- Votumumab (HUMASPECT ®) | Colorectal tumors |
| Frizzled receptor | Vantictumab | cancer |
| Le $^y$ | hu3S193 and IgN311 | Breast, colon, lung and prostate tumors |
| VEGF | Bevacizumab (AVASTIN ®) | Tumor vasculature |
| VEGFR | IM-2C6 and CDP791 | Epithelium-derived solid tumors |
| Integrin αVβ3 | Etaracizumab (ABEGRIN ®), intetumumab | Tumor vasculature |
| Integrin α5β1 | Volociximab | Tumor vasculature |
| EGFR | Cetuximab (ERBITUX ®), panitumumab (VECTIBIX ®), nimotuzumab, necitumumab, zalutumumab, imgatuzumab, matuzumab, and 806 | Glioma, lung, breast, colon, and head and neck tumors |
| EGFL7 | Parsatuzumab | Cancer cells |
| ERBB2 | Trastuzumab (HERCLON ®; HERCEPTIN ®) and pertuzumab (PERJETA ®; OMNITARG ®) | Breast, colon, lung, ovarian and prostate tumors |
| ERBB3 | Duligotumab, MM-121 | Breast, colon, lung, ovarian and prostate, tumors |
| Fibronectin | Radretumab | antineoplastic |
| HGF | Rilotumumab, ficlatuzumab | Solid tumors |
| HER3 | Patritumab | cancer |
| LOXL2 | Simtuzumab | fibrosis |

TABLE 1-continued

Exemplary therapeutic monoclonal antibodies

| Antigen | mAb<br>murine: -tumomab;<br>chimeric: -tuximab;<br>humanized: -tuzumab<br>human: -tumumab | Target Tumor/Disease |
|---|---|---|
| MET | AMG 102, METMAB and SCH 900105 | Breast, ovary and lung tumors |
| IGF1R | Cixutumumab, dalotuzumab, figitumumab, ganitumab, robatumumab, teprotumumab, AVE1642, IMC-A12, MK-0646, R1507, and CP 751871 | Glioma, lung, breast, head and neck, prostate and thyroid cancer |
| IGLF2 | Dusigitumab | |
| EPHA3 | KB004 and IIIA4 | Lung, kidney and colon tumors, melanoma, glioma and hematological malignancies |
| FR-alpha | Farletuzumab | Ovarian cancer |
| phosphatidyl-serine | Bavituximab | Cancer cells |
| Syndecan 1 | Indatuximab ravtansine | |
| SLAMF7 (CD319) | Elotuzumab | Multiple myeloma |
| TRAILR1 | Mapatumumab (HGS-ETR1) | Colon, lung and pancreas tumors and haematological malignancies |
| TRAILR2 | Conatumumab, lexatumumab, mapatumumab, tigatuzumab, HGS-ETR2 and CS-1008 | cancer |
| RANKL | Denosumab (XGEVA ®) | Prostate cancer and bone metastases |
| FAP | Sibrotuzumab, and F19 | Colon, breast, lung, pancreas, and head and neck tumors |
| vimentin | Pritumumab | Brain cancer |
| Tenascin | 81C6 | Glioma, breast and prostate tumors |

IV. Antibody-Dependent Cytotoxicity

In vitro assays are commonly employed for purposes such antibody-dependent cellular cytotoxicity (ADCC) assays. Typically target cells are loaded with an indicator material (such as $^{51}Cr$), and the indicator-loaded target cells are treated with the antibody to be evaluated. The resulting cells are exposed to NK effector cells as described herein. Lysis of the target cells is indicated by the release of the indicator material into the assay supernatant where its concentration can be measured by a suitable method such as scintillation counting ($^{51}Cr$) or fluorescence intensity or lifetime determination. Efficacy can likewise be assessed by the measurement of surrogate indicators such as cytokine release by the NK cells; the up-regulation of NK cell activation markers, such as CD25, CD69 and/or CD95L; activation of NK cell transcription factors, such as NF-AT or NF-κB; or the activation of caspases or other markers of apoptosis in the target cells. CD16-deficient parental NK cells (such as non-transfected NK cells) serve as a control because they permit differentiating between ADCC-mediated cytotoxicity and other cytolytic effects that NK cells exert on the target cells.

The preferred target cells in ADCC assays are ones that express an antigen that is appropriate to the antibody being evaluated and that have low susceptibility to lysis by the parental NK cell line. If such a target cell line is not conveniently available, other suitable cell lines, such as the ovarian carcinoma line SKOV-3 (Tam et al., 1999, Characterization of genetically altered, interleukin 2-independent natural killer cell lines suitable for adoptive cellular immunotherapy, Hum. Gene Ther. 10:1359-73) can sometimes be used if they express the specific antigen required.

Among the cell lines that have been demonstrated to be suitable for use in assays of ADCC-mediated cytotoxicity are U373MG and T98G (Komatsu et al., 1998, Relation of natural killer cell line NK-92-mediated cytolysis (NK-92-lysis) with the surface markers of major histocompatibility complex class I antigens, adhesion molecules, and Fas of target cells, Oncol. Res. 10:483-89); AML-193 (myeloid) and SR-91 (lymphoid progenitor) (Gong et al., 1994, Characterization of a human cell line (NK-92) with phenotypical and functional characteristics of activated natural killer cells, Leukemia 8:652-58); and ALL1 and REH (B-cell acute lymphocytic leukemia) (Reid et al., 2002, Differential killing of pre-B acute lymphoblastic leukaemia cells by activated NK cells and the NK-92 ci cell line, Clin. Exp. Immunol. 129:265-71).

In some instances, it can be advantageous to block known activating receptors on NK cells, for example, prior to administration of NK cells to a subject. Such methods and agents are well-known; see for example, Pende et al., 1999, Identification and molecular characterization of NKp30, a novel triggering receptor involved in natural cytotoxicity mediated by human natural killer cells, J. Exp. Med. 190: 1505-16; Pessino et al., 1998, Molecular cloning of NKp46: a novel member of the immunoglobulin superfamily involved in triggering of natural cytotoxicity, J. Exp. Med. 188:953-60; Vitale et al., 1998, NKp44, a novel triggering surface molecule specifically expressed by activated natural killer cells, is involved in non-major histocompatibility complex-restricted tumor cell lysis, J. Exp. Med. 187:2065-72. For example, masking antibodies can be used (Pessino et al., 1998). In one example, a fragment of an anti-CD38 antibody can be used to mask CD38 on NK cells, prior to administration of NK cells and an anti-CD38 antibody (such as daratumumab) to a subject (discussed in more detail below).

V. Treating or Inhibiting a Tumor or Hyperproliferative Disorder

Disclosed herein are methods of treating a subject with a tumor or hyperproliferative disease with the modified NK cells described herein in combination with a therapeutic monoclonal antibody (such as an anti-tumor antigen or anti-cancer antibody). The modified NK cells described herein can be administered either to animals or to human subjects.

The modified NK cells described herein can be incorporated into pharmaceutical compositions. Such compositions typically include a population of modified NK cells and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (Gennaro, 2000, *Remington: The science and practice of pharmacy*, Lippincott, Williams & Wilkins, Philadelphia, PA). Examples of such carriers or diluents include, but are not limited to, water, saline, Ringer's solutions, dextrose solution, and 5% human serum albumin. Liposomes and non-aqueous vehicles such as fixed oils may also be used. Supplementary active compounds can also be incorporated into the compositions.

In some examples, the composition includes about $10^4$ to $10^{12}$ of the modified NK cells (for example, about $10^4$-$10^7$ cells, about $10^6$-$10^9$ cells, or about $10^8$-$10^{12}$ cells). For example, the composition may be prepared such that about $10^6$ to $10^{10}$ modified NK cells/kg are administered to a subject. In some examples, the compositions include pharmaceutically acceptable carriers and/or one or more additional agents. Actual methods for preparing administrable compositions are known or apparent to those skilled in the art and are described in more detail in such publications as *Remington: The Science and Practice of Pharmacy*, The University of the Sciences in Philadelphia, Editor, Lippincott, Williams, & Wilkins, Philadelphia, PA, 21$^{st}$ Edition (2005).

In some examples, the methods include treating or inhibiting a hyperproliferative disorder, such as a hematological malignancy or a solid tumor. Examples of hematological malignancies include leukemias, including acute leukemias (such as 11923-positive acute leukemia, acute lymphocytic leukemia, acute myelocytic leukemia, acute myelogenous leukemia and myeloblastic, promyelocytic, myclomonocytic, monocytic and erythroleukemia), chronic leukemias (such as chronic myelocytic (granulocytic) leukemia, chronic myelogenous leukemia, and chronic lymphocytic leukemia), T-cell large granular lymphocyte leukemia, polycythemia vera, lymphoma, diffuse large B-cell lymphoma, Hodgkin's lymphoma, non-Hodgkin's lymphoma (indolent and high grade forms), mantle cell lymphoma, follicular cell lymphoma, multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, phcochromocytoma, sebaceous gland carcinoma, papillary carcinoma, papillary adenocarcinoma, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pincaloma, hemangioblastoma, acoustic neuroma, oligodendroglioma, meningioma, melanoma, neuroblastoma, and retinoblastoma).

In particular examples, hematological malignancies that can be inhibited or treated by the methods disclosed herein include but are not limited to multiple myeloma, chronic lymphocytic leukemia, acute lymphocytic leukemia, acute myeloid leukemia, chronic myeloid leukemia, pro-lymphocytic/myelocytic leukemia, plasma cell leukemia, NK cell leukemia, Waldenstrom macroglobulinemia, Hodgkin's lymphoma, non-Hodgkin's lymphoma, mantle cell lymphoma, diffuse large B-cell lymphoma, and follicular lymphoma. In additional particular examples, solid tumors that can be treated or inhibited by the methods disclosed herein include lung carcinoma, prostate cancer, pancreatic cancer (for example, insulinoma), breast cancer, colorectal adenocarcinoma or squamous cell carcinoma, neuroblastoma, testicular cancer (such as seminoma), and ovarian cancer. In particular examples, the cells of the hematological malignancy or the solid tumor express or overexpress CD38. In one specific example, the subject has multiple myeloma.

One of ordinary skill in the art can select an appropriate therapeutic (e.g., anti-cancer) mAb (such as a mAb listed in Table 1) to administer to the subject with the modified NK cells described herein. For example, a subject with multiple myeloma is treated with an anti-CD38 antibody (such as daratumumab) and modified NK cells expressing CD16-V158. A subject with breast cancer can be treated with an anti-EGFR antibody (such as rituximab or panitutumab) or an anti-ERBB2 antibody (such as trastuzumab) and modified NK cells expressing CD16-V158. In another example, a subject with non-Hodgkins lymphoma is treated with an anti-CD20 antibody (such as rituximab or ofatumumab) and modified NK cells expressing CD16-V158 and/or CCR7. In further examples, a subject with a hematological malignancy that resides at least in part in the bone marrow (such as acute or chronic leukemias, multiple myeloma or Hodgkin's or non-Hodgkin's lymphoma) is treated with an antibody targeting the hematological malignancy shown in Table 1 and modified NK cells expressing CD16-V158 and/or VLA-4 or LFA-1.

In vivo treatment of a subject is initiated by administration of a targeting antibody (such as those shown in Table 1) prior to, or concurrently with, the administration of the modified NK cells disclosed herein. Administration is typically via intravenous or intraperitoneal infusion, although direct injection into solid tumors or other such focal lesions can also be used. A split-dose regimen can be utilized, particularly when a cytokine (such as IL-2 or IL-15) is not being co-administered, in order to maintain a high level of active, transduced NK cells in the subject. In some cases, administering the antibody by infusion and the transduced cells by direct injection can be advantageous. The efficacy of the treatment is generally assessed by lesion reduction/clearance, cytokine profile or other physiological parameters.

In particular examples, the subject is administered an effective dose of an antibody before, after, or substantially simultaneously with the population of modified NK cells. In some examples, the subject is administered about 0.1 mg/kg to about 100 mg/kg of the antibody (such as about 0.5-10 mg/kg, about 1-20 mg/kg, about 10-50 mg/kg, about 20-100 mg/kg, for example, about 0.5 mg/kg, about 1 mg/kg, about 2 mg/kg, about 3 mg/kg, about 4 mg/kg, about 5 mg/kg, about 8 mg/kg, about 10 mg/kg, about 16 mg/kg, about 20 mg/kg, about 24 mg/kg, about 36 mg/kg, about 48 mg/kg, about 60 mg/kg, about 75 mg/kg, or about 100 mg/kg). An effective amount of the antibody can be selected by a skilled clinician, taking into consideration the particular antibody, the particular tumor or disorder, the general condition of the subject, any additional treatments the subject is receiving or has previously received, and other relevant factors. The subject is also administered a population of modified NK cells described herein. In some examples, about $10^6$ to $10^{10}$ modified NK cells/kg (such as about $10^6$, $10^7$, $10^8$, $10^9$, or $10^{10}$ cells/kg) are administered to a subject. Both the antibody and the population of modified NK cells are typically administered parenterally, for example intravenously; however, injection or infusion to a tumor or close to a tumor (local administration) or administration to the peritoneal cavity can also be used. One of skill in the art can determine appropriate routes of administration.

Figure 6:
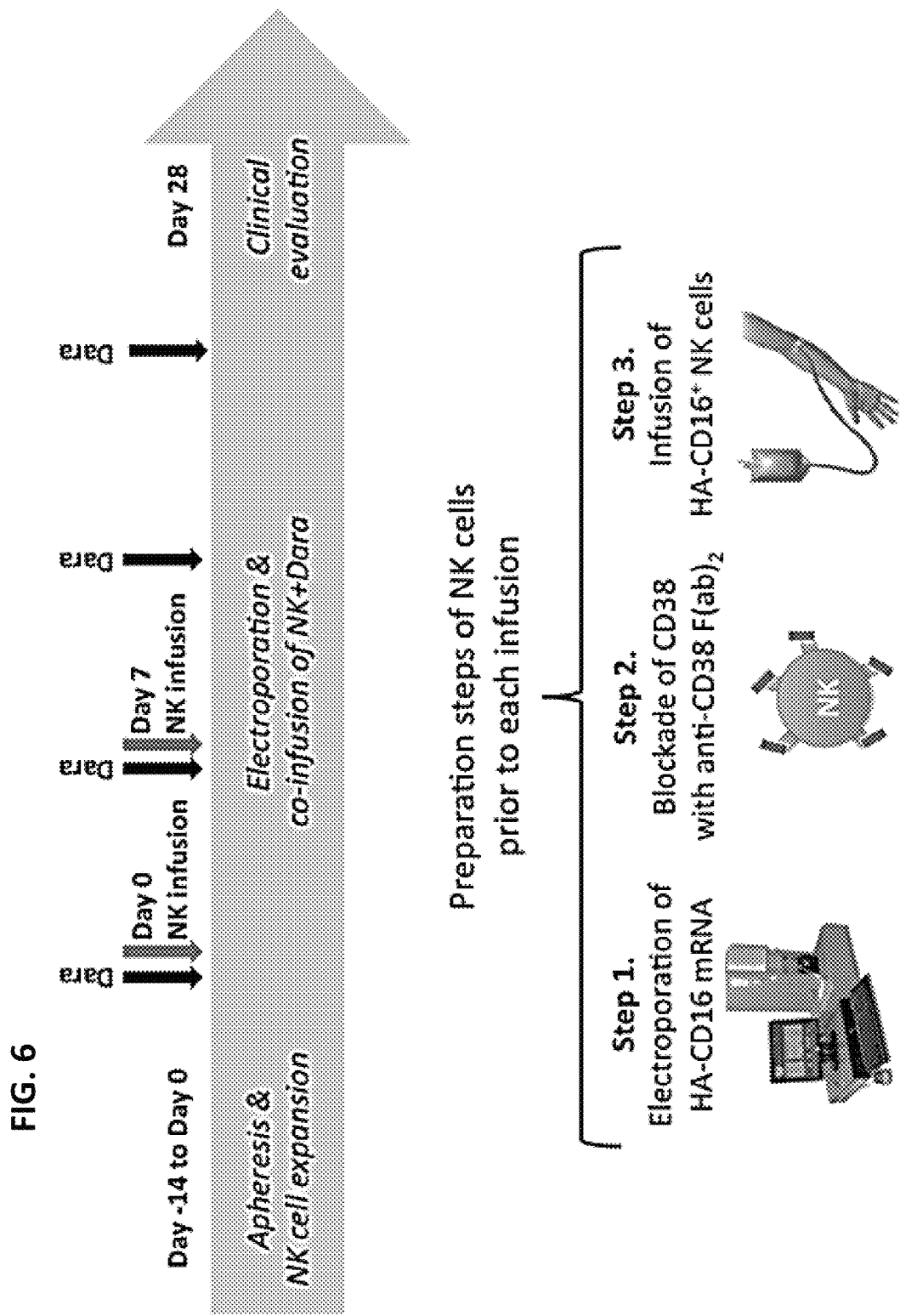
FIG. 6 is a schematic outline of an exemplary clinical procedure using electroporation of NK cells with HA-CD16 to improve the outcome of multiple myeloma patients treated with Daratumumab. A similar protocol can be used to treat patients with other antibodies, except that the step of blockade of CD38 on the NK cells is omitted.

Multiple doses of the population of modified NK cells and/or the antibody can be administered. For example, the population of modified NK cells can be administered every other day, twice per week, weekly, every other week, every three weeks, monthly, or less frequently. Similarly, the antibody can be administered every other day, twice per week, weekly, every other week, every three weeks, monthly, or less frequently. In some examples, the population of modified NK cells and the antibody are administered on the same schedule or on a staggered schedule. A specific example of an administration schedule is shown in FIG. 6; however, a skilled clinician can select alternative schedules based on the subject, the condition being treated, the previous treatment history, and other factors.

The population of modified NK cells is administered to the subject before, after, or substantially simultaneously with the antibody. In particular examples, the population of modified NK cells is administered after the antibody, for example within 1 hour to three weeks (such as within about 1-48 hours, about 2-24 hours, about 2-10 hours, about 12-72 hours, about 1-5 days, about 7-21 days, about 10-14 days, for example, within about 2 hours, about 4 hours, about 6 hours, about 8 hours, about 12 hours, about 24 hours, about 48 hours, about 3 days, about 4 days, about 5 days, about 6 days, about 7 days, about 10 days, about 14 days, or about 21 days) of the administration of the antibody. In one specific example, the population of modified NK cells is administered to the subject within about 1-8 hours (such as within about 1-4 hours, about 2-6 hours, about 4-6 hours, or about 5-8 hours) of the administration of the antibody. In some examples, this administration pattern is repeated two times per week for at least two weeks or once weekly for at least two weeks. In further examples, additional doses of the antibody are administered without administering modified NK cells, for example additional weekly doses of the antibody for at least one or two weeks (e.g., as shown in FIG. 6).

In some examples, the subject (such as a subject with a tumor or hyperproliferative disorder) is also administered one or more additional treatments, such as one or more chemotherapeutic agents and/or radiation therapy. One of skill in the art can select additional chemotherapeutic agents for administration to a subject in combination with the modified NK cells and antibodies described herein. Such agents include alkylating agents, such as nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine); antimetabolites such as folic acid analogs (such as methotrexate), pyrimidine analogs (such as 5-FU or cytarabine), and purine analogs, such as mercaptopurine or thioguanine; or natural products, for example vinca alkaloids (such as vinblastine, vincristine, or vindesine), epipodophyllotoxins (such as ctoposide or teniposide), antibiotics (such as dactinomycin, daunorubicin, doxorubicin, bleomycin, plicamycin, or mitocycin C), and enzymes (such as L-asparaginase). Additional agents include platinum coordination complexes (such as cis-diamine-dichloroplatinum II, also known as cisplatin), substituted ureas (such as hydroxyurea), methyl hydrazine derivatives (such as procarbazine), and adrenocrotical suppressants (such as mitotane and aminoglutethimide); hormones and antagonists, such as adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs include adriamycin, melphalan (Alkeran®) Ara-C (cytarabine), carmustine, busulfan, lomustine, carboplatinum, cis-platinum, cyclophosphamide (Cytoxan®), daunorubicin, dacarbazine, 5-fluorouracil, fludarabine, hydroxyurea, idarubicin, ifosfamide, methotrexate, mithramycin, mitomycin, mitoxantrone, nitrogen mustard, paclitaxel (or other taxanes, such as docetaxel), vinblastine, vincristine, VP-16, while newer drugs include gemcitabine (Gemzar®), trastuzumab (Herceptin®), irinotecan (CPT-11), leustatin, navelbine, rituximab (Rituxan®) imatinib (STI-571), Topotecan (Hycamtin®), capecitabine, ibritumomab (Zevalin®), and calcitriol.

In additional examples, the subject is administered one or more cytokines (such as IL-2, IL-15, IL-21, and/or IL-12) to support survival and/or growth of NK cells. The cytokine(s) can be administered before, after, or substantially simultaneously with the NK cells. In some examples, the cytokine(s) can be administered after the NK cells. In one specific example, the cytokine(s) is administered to the subject within about 1-8 hours (such as within about 1-4 hours, about 2-6 hours, about 4-6 hours, or about 5-8 hours) of the administration of the NK cells.

A. Treatment of a Subject with Multiple Myeloma

In particular examples, the modified NK cells disclosed herein are utilized to treat a subject with multiple myeloma. Multiple myeloma (also known as plasma cell myeloma, myelomatosis, or Kahler's disease), is a cancer of plasma cells, a type of white blood cell normally responsible for producing antibodies. In multiple myeloma, collections of abnormal plasma cells accumulate in the bone marrow, where they interfere with the production of normal blood cells. Most cases of multiple myeloma also feature the production of a paraprotein—an abnormal antibody which can cause kidney problems. Bone lesions and hypercalcemia (high blood calcium levels) are also often encountered.

Multiple myeloma develops in 6.1 per 100,000 people per year. It is more common in men and, for unknown reasons, is twice as common in African-Americans as it is in European-Americans. With conventional treatment, median survival is 3-4 years, which may be extended to 5-7 years or longer with advanced treatments. Multiple myeloma is the second most common hematological malignancy in the U.S.

(after non-Hodgkin lymphoma), and constitutes 1% of all cancers. The five year survival rate is 45%.

Multiple myeloma (MM) remains an incurable hematological malignancy. Daratumumab (Dara) is a CD38 specific monoclonal IgG1 antibody that has shown promise in early MM clinical trials. The major mechanism through which daratumumab kills CD38+ myeloma cells is ADCC mediated by CD16+ NK cells. However, NK cells also express CD38, and their numbers decline in circulation following daratumumab treatment, likely limiting the therapeutic potential of this antibody.

In some examples, a subject with multiple myeloma is treated with the modified NK cells expressing CD16-V158 protein disclosed herein. In particular examples, the modified NK cells are prepared from NK cells expanded from the subject with multiple myeloma. In other examples, the modified NK cells are prepared from NK cells expanded from a donor (such as an HLA matched, partially HLA matched, or HLA mismatched donor). Prior to administering the modified CD16-V158 NK cells to the subject, the population of modified NK cells is contacted with an anti-CD38 antibody fragment (such as anti-CD38 F(ab)2) or protein G to block CD38 on the NK cells. Blockade of CD38 on NK cells using anti-CD38 F(ab)2 or protein G can be carried out as described in Example 6 or as in Intl. Pat. App. Nos. PCT/US2015/035831 and PCT/US2015/035832, both of which are incorporated herein by reference in their entirety. The CD38-blocked modified NK cells are then administered to the subject with multiple myeloma in conjunction with daratumumab treatment. In some examples, daratumumab is administered to the subject and the CD38-blocked modified NK cells are administered to the subject within about 2-8 hours of the daratumumab treatment. The daratumumab/CD38-blocked modified NK cell treatment can be repeated, for example on a weekly basis as needed. An exemplary protocol is shown in FIG. 6.

In some examples, the subject with multiple myeloma is also administered one or more additional treatments, such as one or more chemotherapeutic agents and/or radiation therapy. For example, the subject is treated as described herein, and is also administered an immunomodulatory agent (such as lenalidomide, thalidomide, or pomalidomide), a proteasome inhibitor (such as bortezomib, carfilzomib, salinosporamide A, epoxomicin, marizomib (NPI-0052), ixazomib (MLN9708), CEP18770, or oprozomib (ONX0912)), steroids (such as dexamethasone, prednisone, prednisolone, or methylprednisolone), and/or other chemotherapeutics (such as melphalan). In a particular example, a subject with multiple myeloma may be administered a combination therapy with the modified NK cells and an anti-CD38 antibody, such as daratumumab (or another anti-CD38 antibody) in combination with lenalidomide, alone, or in combination with bortezomib. In other examples, the subject may be administered daratumumab (or another anti-CD38 antibody), lenalidomide, bortezomib, and dexamethasone, or daratumumab (or another anti-CD38 antibody), melphalan, prednisone, and bortezomib.

The present disclosure is illustrated by the following non-limiting Examples.

EXAMPLE 1

Materials and Methods

Cell lines and reagents: The K562, MM.1S and CD20+ 721.221 cell lines were obtained from ATCC (Manassas, VA) and propagated in RPMI 1640 supplemented with 10% heat-inactivated FBS (Sigma-Alrich) and 2 mM Glutamine (Life Technologies). The following reagents were used: anti-CD56 (NCAM-1), anti-CD3 (UCHT1), anti-CD16 (3G8), anti-NKG2D (1D11), anti-TRAIL (RIK-2), anti-NKp30 (p30-15), anti-NKp46 (29A1.4), IgG1 (MOPC21), Annexin V and 7-AAD from Becton Dickinson (BD). Anti-KIR2DL1/DS1 (EB6), anti-KIR2DL2/3/DS2 (GL183) and anti-NKG2A (Z199) from Beckman Coulter. The anti-CD107a (H4A3), anti-KIR3DL1 (Dx9), anti-CD57 (HCD57), anti-2B4 (C1.7), anti-CD34 (581), anti-CCR7 (G043H7), IgG2a (MOPC-173), and BV650-streptavidin from Biolegend. The anti-Lir-1 (HP-F1) from eBioscience. The anti-NKG2C (134591) from R&D Systems. LIVE/DEAD viability marker from Life Technologies. Biotinylated anti-KIR3DL2 (Dx31) from UCSF. Rituximab (Rituxan) from Genentech. Off-the-shelf eGFP mRNA and custom made CD34, CD16, CCR7 mRNAs from TriLink Biotechnology.

NK cell expansion: NK cells expanded ex vivo for 11 to 15 days were isolated from healthy donor PBMC using the NK cell Isolation Kit from Miltenyi and combined in G-Rex flasks (Wilson Wolf Manufacturing) with irradiated EBV-SMI-LCL cells at a ratio of 1:10 in NK cell media (X-VIVO 20 (Lonza) supplemented with 10% heat-inactivated human AB plasma (Sigma Aldrich) and 500 IU/mL of recombinant human IL-2 (Roche)) (Childs and Berg, *Hematology, The Education Program* 2013:234-246, 2013). The cells were cultured at 37° C., 6.5% $CO_2$. Half of the media was replaced with fresh NK cell media 5 days into the expansion. NK cells were thereafter counted and adjusted to $0.5-1\times10^6$ cells/ml every 48 hours from day 7 until utilized in experiments.

Electroporation of NK cells: NK cells were electroporated using the MAXCYTE® GT® Transfection System. In brief, cells were first collected and washed in electroporation buffer (HyClone). They were then mixed with mRNA in a total volume of 100 μl and transferred to an OC-100 cuvette. Electroporation was conducted using an optimized program for NK cells. Cells were then transferred to one well of a 48 well plate and incubated at 37° C., 6.5% $CO_2$ for 20 minutes before being resuspended in NK cell media and transferred to culture flasks.

Cytotoxicity assay: NK cells were co-cultured at a ratio of 1:1 with either $^{51}$Cr-labeled K562 cells or MM.1S cells in a final volume of 200 μl in 96-well plates at 37° C. and 5% $CO_2$. After four hours, supernatant was harvested onto a Luma plate. Counts were measured using a Perkin Elmer 1450 Microbeta Counter and specific target lysis was calculated using the following formula: ((NK cell-induce $^{51}$Cr-release−spontaneous $^{51}$Cr-release)/(maximum $^{51}$Cr-release−spontaneous $^{51}$Cr-release)×100).

NK cell migration assay: Migration assays were performed using 24 well plates with Corning Transwell® inserts. 600 μl of serum free X-VIVO 20 containing various concentrations of recombinant human CCL19 (Biolegend) was added to the bottom chambers and $5\times10^4$ NK cells in 100 μl of serum free X-VIVO 20 media without CCL19 was added to the top chambers. The plate was incubated for 2 hours at 37° C. in 5% $CO_2$ before transwell membranes were removed and cells in the bottom chamber were harvested. The amount of migrated cells was quantified on a Wallac 1420 Microplate Reader (Perkin Elmer) using the CYQUANT™ kit (Life Technologies). Cells plated straight to the bottom chamber were used as maximum control and the proportion of migrated cells was calculated as a percent of total cells initially added to each well.

NK cell degranulation assay: NK cells were co-cultured with 721.221 cells at a ratio of 1:1 in 96-well plates at 37° C. and 5% $CO_2$ with or without Rituximab. After one hour, cells were stained with cell surface mAbs and a viability marker for 15 minutes on ice, followed by washes and fixation in 1% paraformaldehyde (MP Biomedicals) in PBS. Cells were acquired on a BD LSR II Fortessa.

Data and statistical analysis: Flow cytometry data was analyzed using the FLOWJO® software (Treestar Inc.). Graphs and statistical analyses were performed with GRAPHPAD® PRISM (GraphPad Software Inc.). *$p<0.05$, **$p<0.01$.

EXAMPLE 2

Transfection of NK Cells

This example describes transfection of NK cells with green fluorescent protein or CD34, and evaluation of the viability and cytotoxicity of the transfected cells.

Figure 1B:
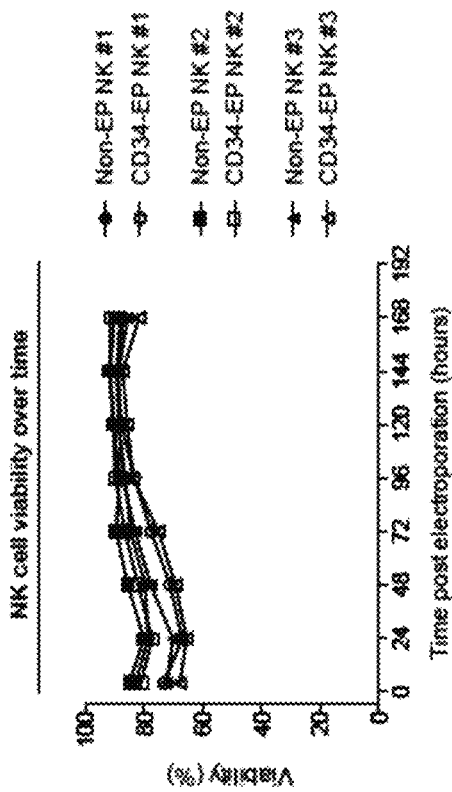
Figure 1C:
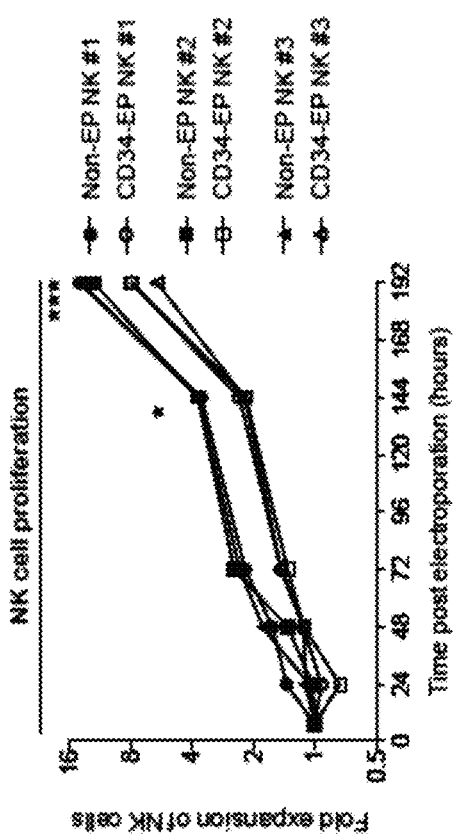
Figure 1D:
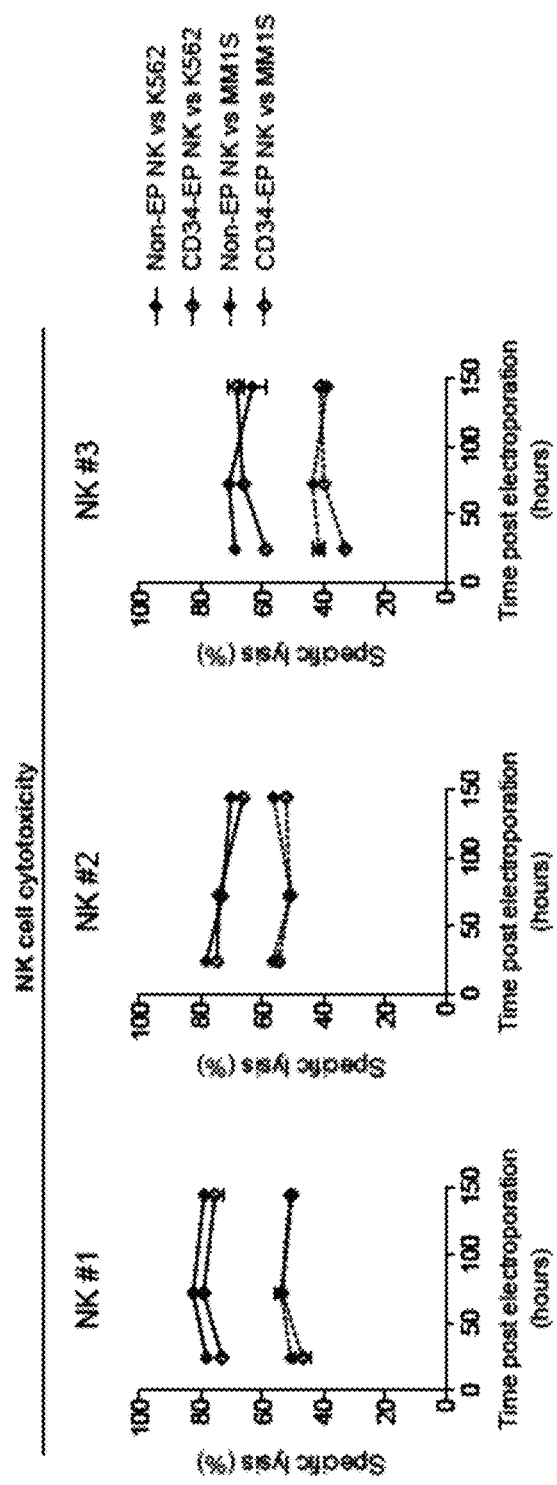

The transfection efficacy, viability, proliferation, and function of ex vivo expanded NK cells following mRNA electroporation was evaluated. Using the scalable cGMP-compliant MAXCYTE® GT transfection system and NK cells expanded utilizing methods from an ongoing Phase I clinical trial, highly reproducible rapid GFP protein expression was obtained in nearly 100% of eGFP mRNA electroporated NK cells (FIG. 1A). GFP expression was detectable in proliferating NK cells for up to three weeks, with expression in >95% of cells for the first 7-9 days after gene delivery, and had no deleterious effects on cell viability. Since GFP represents an intracellular molecule with a long half-life, the capacity of this transfection technique to induce expression of selected molecules on the surface of NK cells was evaluated. Electroporation of NK cells with mRNA coding for the cell surface marker CD34 (SEQ ID NO: 7) led to surface expression for up to seven days, with peak expression occurring approximately 24 hours after electroporation (FIG. 1B). As with GFP, no significant impact on viability was observed following electroporation. Although electroporated NK cells maintained their capacity to proliferate in vitro, there was a small reduction in proliferation compared to non-electroporated controls (FIG. 1C). NK cell cytotoxicity, as assessed by their ability to kill K562 cells and the multiple myeloma cell line MM.1S, remained high and was unaffected by electroporation compared to controls (FIG. 1D).

Figure 2B:
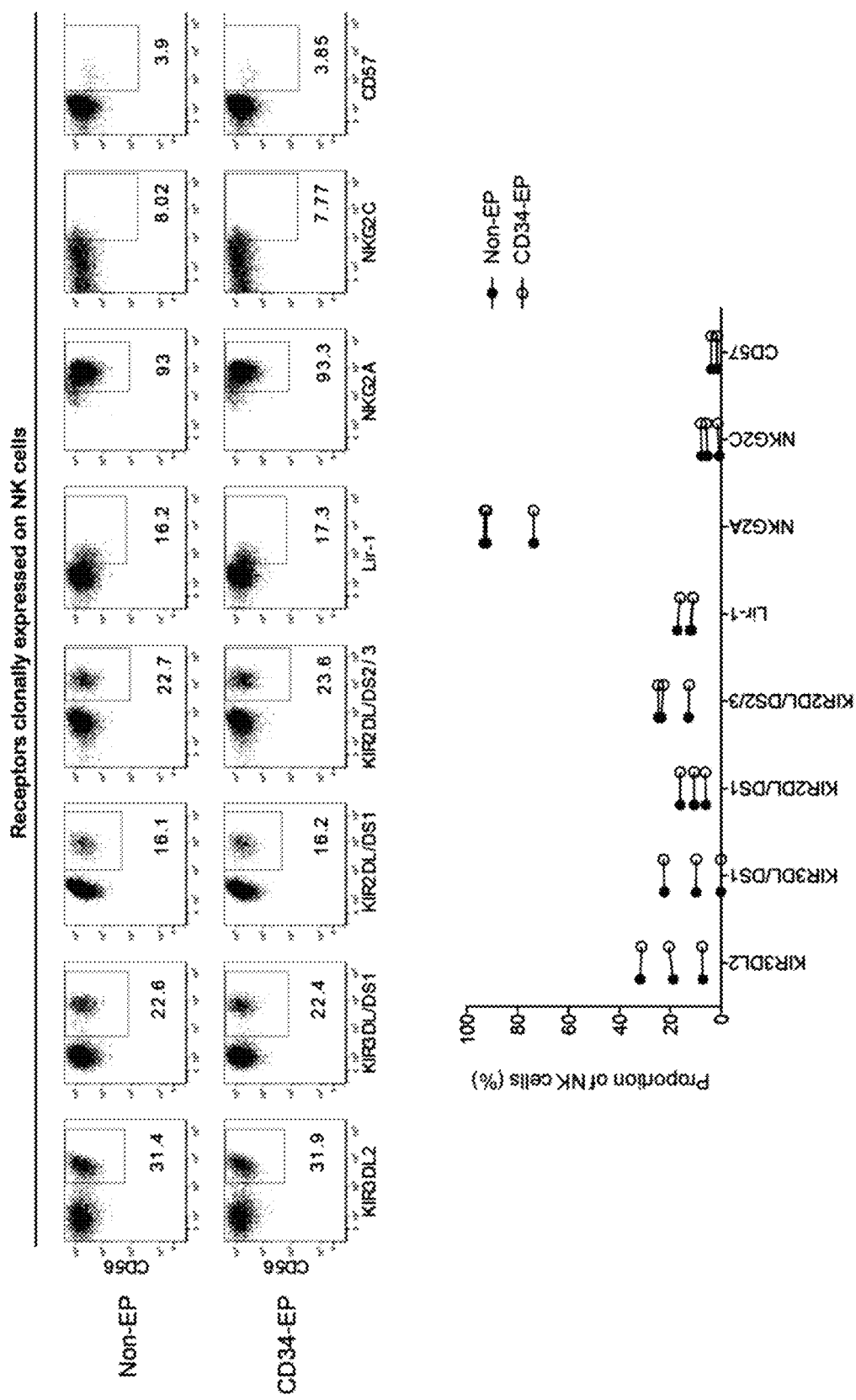

As electroporation of NK cells potentially could lead to unintended phenotypic alternations that perturb NK cell activation and target specificity, high-resolution flow cytometry was performed to evaluate the phenotype of CD34 mRNA electroporated NK cells compared to controls. With the exception of slight decreases in NKp30, 2B4 and TRAIL, there were no significant alterations in the surface expression of any of the fifteen activating and inhibitory NK cell receptors in CD34 mRNA electroporated NK cells compared to controls 24 hours after electroporation (FIGS. 2A and 2B). Daily flow cytometry analysis showed no additional phenotypic changes occurred during the first 6 days following electroporation with CD34 mRNA.

EXAMPLE 3

Expression of CCR7 in NK Cells

This example describes transfection of NK cells with chemokine receptor CCR7 and evaluation of their migration towards CCR7 ligands.

Figure 3A:
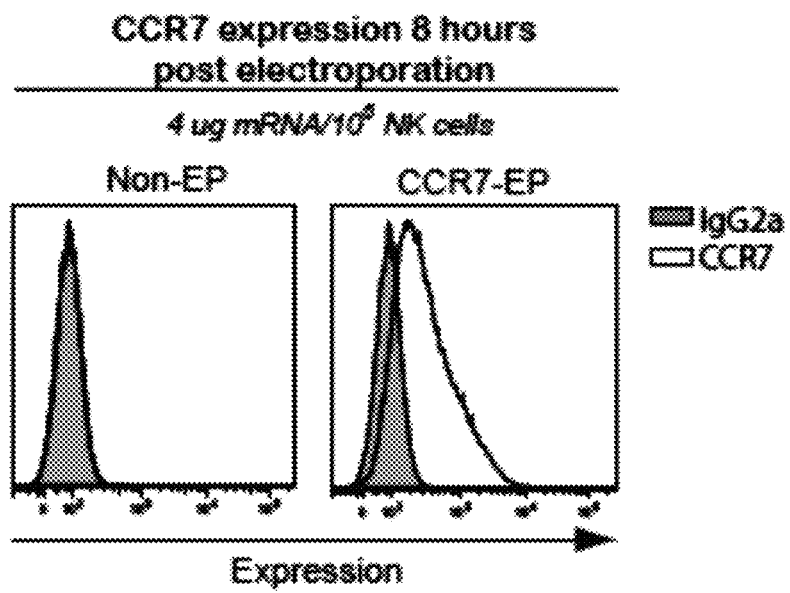
FIGS. 3A-3D are a series of panels showing CCR7 expression and migration capacity of clinical-grade ex vivo expanded NK cells electroporated with CCR7 mRNA.
Figure 3B:
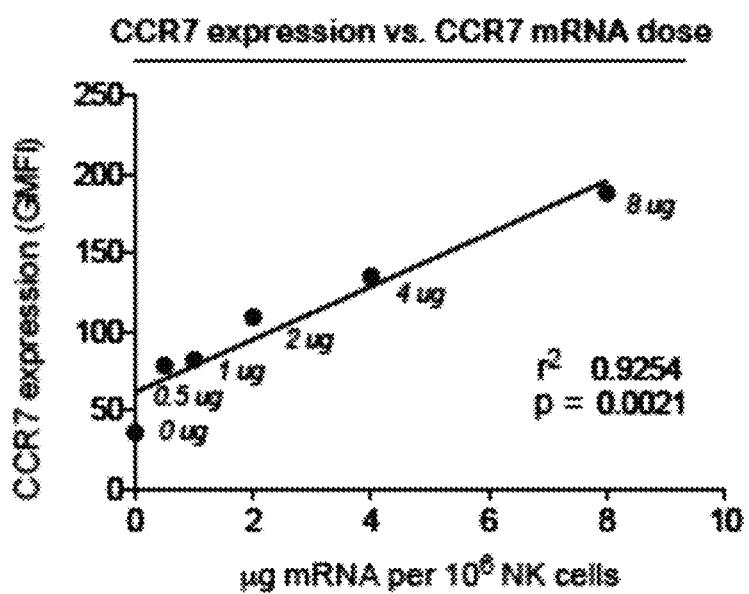
Figure 3C:
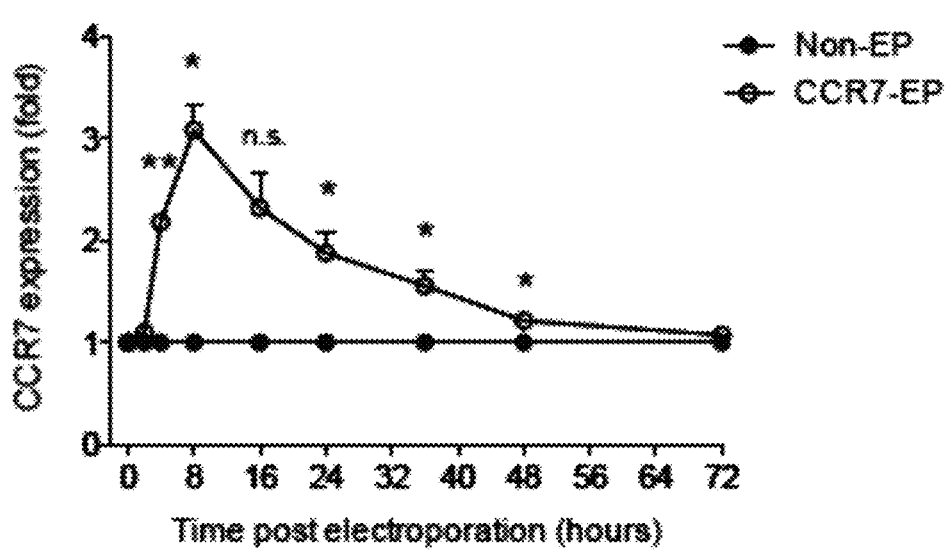
Figure 3D:
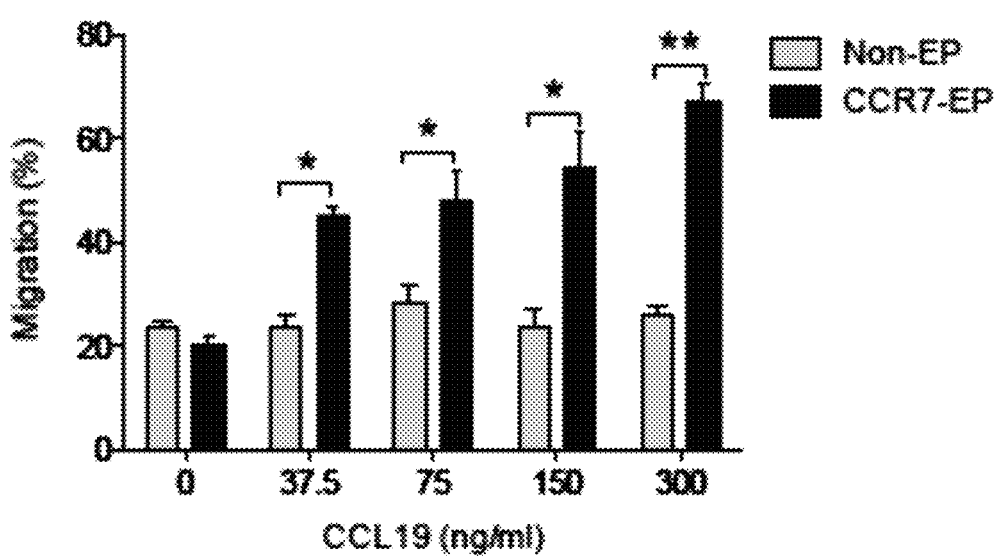

The use of mRNA electroporation to genetically engineer adoptively infused NK cells to improve their homing to selected organs in vivo has not previously been studied. Therefore, NK cells were electroporated with mRNA coding for the chemokine receptor CCR7 (SEQ ID NO: 10), which is known to direct cellular migration to secondary lymphoid tissues, including lymph nodes where hematological malignancies such as lymphoma reside. The CCR7 receptor is normally expressed by only a small subset of resting primary NK cells (primarily the $CD56^{bright}$ NK cell subset), with expression completely disappearing following ex vivo expansion. By electroporating expanded NK cells with increasing concentrations of CCR7 mRNA, a correlation between mRNA dose and CCR7 cell surface expression was established (FIGS. 3A and 3B). Using 4 μg CCR7 mRNA per million NK cells, cell surface expression of CCR7 was sustained for up to 48 hours, with peak expression measured 8 hours following electroporation (FIG. 3C). CCR7 mRNA electroporated NK cells showed marked dose-dependent in vitro migration capacity towards CCL19 and CCL21 (FIG. 3D), whereas non-electroporated NK cells remained incapable of migrating towards the ligand for this chemokine receptor.

EXAMPLE 4

Augmented NK Cell ADCC against Lymphoma Cells by Introduction of High-Affinity CD16-158V Receptor This example describes transfection of NK cells with high-affinity CD16-158V and evaluation of ADCC against lymphoma cells contacted with rituximab.

Figure 4A:
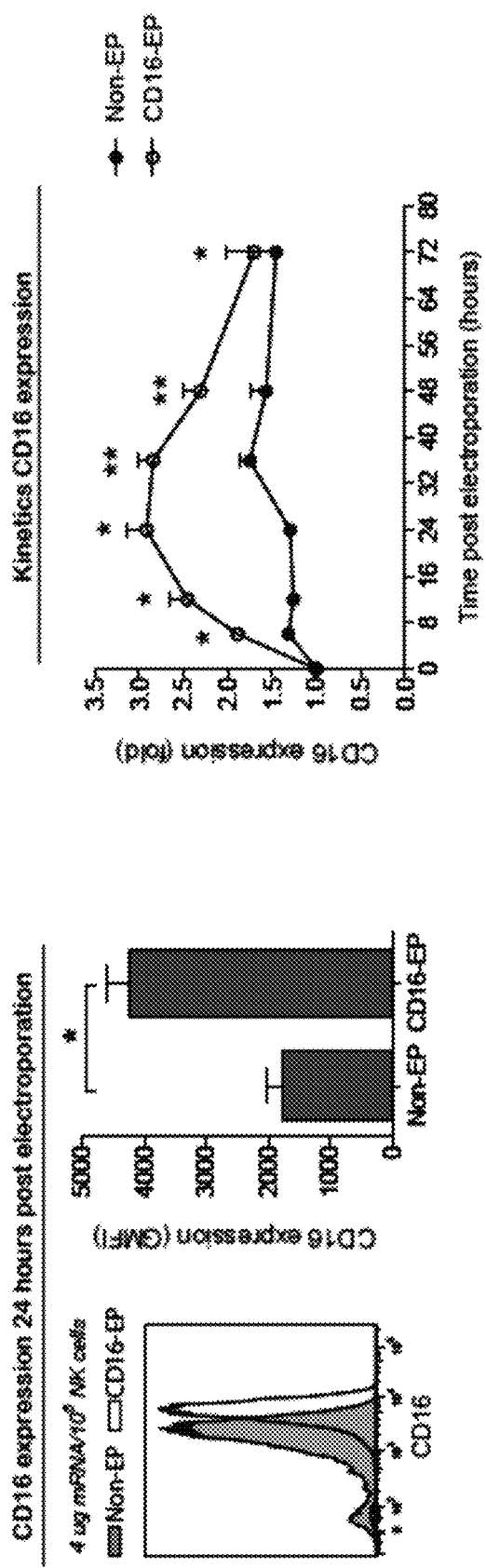
FIGS. 4A-4D are a series of panels showing CD16 expression and ADCC capacity of clinical-grade ex vivo expanded NK cells electroporated with CD16-158V mRNA.

To establish whether this GMP-complaint transfection technique could also be used to improve NK cell cytotoxicity, NK cells obtained from CD16-158F/F donors were transfected with mRNA coding for the high-affinity Fc receptor CD16-158V (SEQ ID NO: 5) in an effort to augment their capacity to induce ADCC against rituximab-coated CD20⁺ B cell lymphoma cells. As shown in FIG. 4A, 24 hours following the electroporation of NK cells with CD16-158V mRNA, cell surface expression of CD16 increased significantly compared to non-electroporated controls. Kinetic studies showed CD16 expression in electroporated cells remained at higher levels than controls for up to 72 hours following electroporation.

Figure 4B:
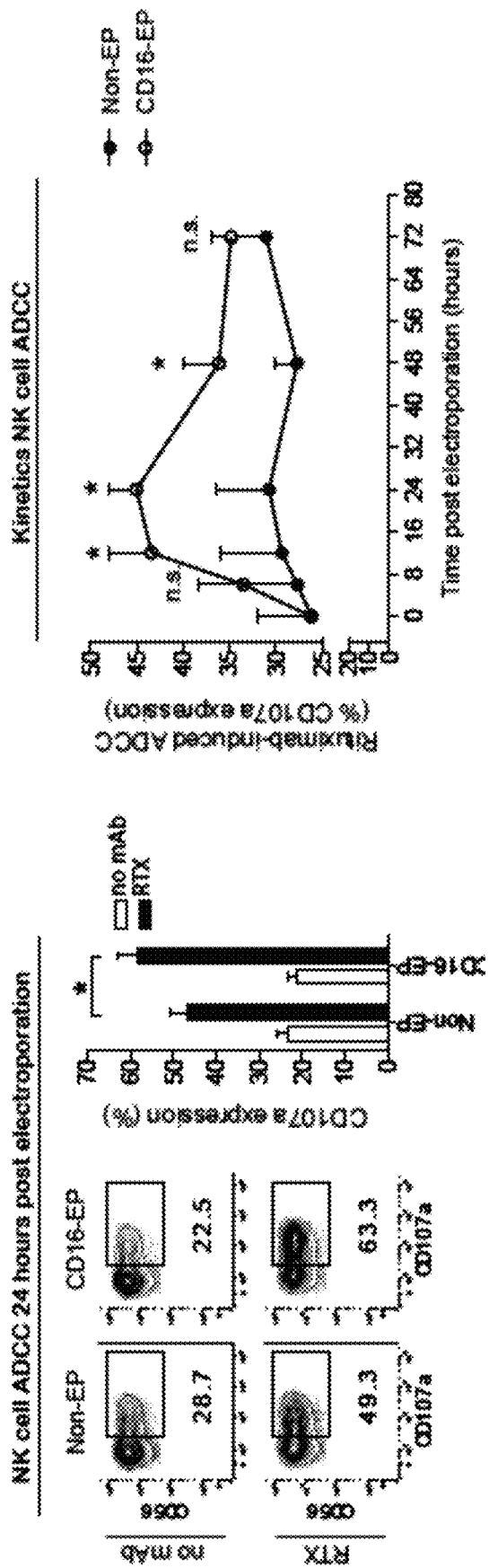
Figure 4C:
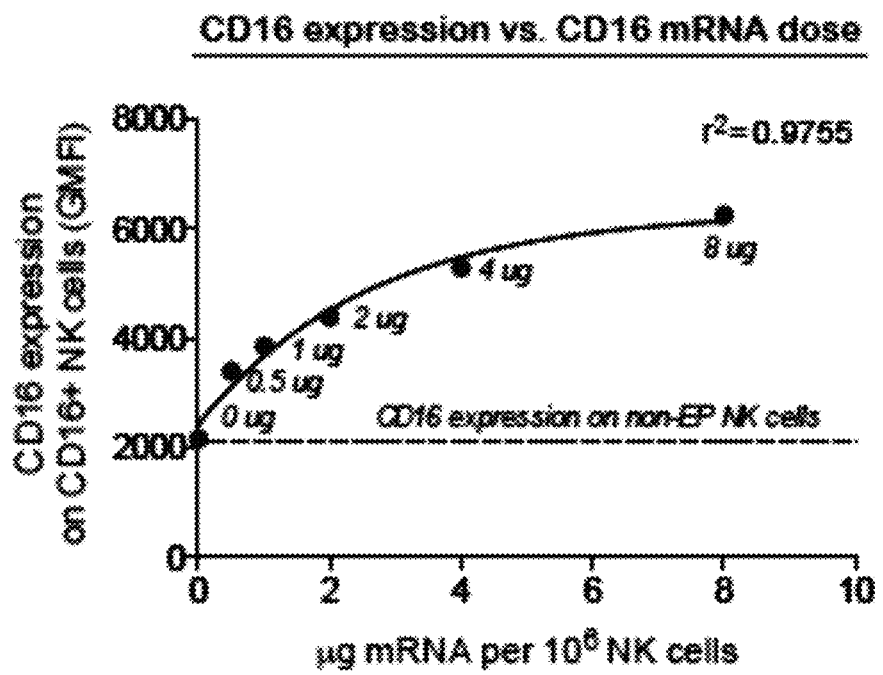
Figure 4D:
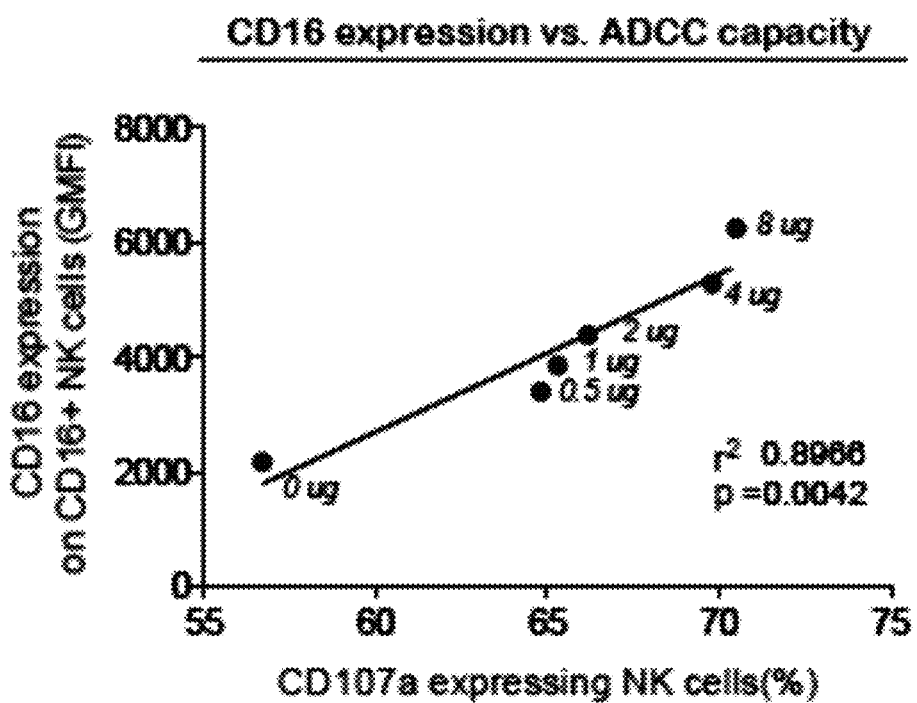

In line with these phenotypic changes, CD16-158V mRNA electroporated NK cells acquired an enhanced ability to mediate ADCC when co-cultured with rituximab-coated EBV-transformed B-cell lymphoma cells compared to controls. This enhanced killing effect against rituximab treated tumor cells persisted for up to 3 days following electroporation (FIG. 4B). By conducting experiments where NK cells were loaded with different concentrations of the CD16-158V mRNA, it was observed that both CD16 expression and ADCC were CD16-158V mRNA dose-dependent (FIGS. 4C and 4D). Taken altogether, these data establish mRNA electroporation as a rapid, efficient, and non-toxic method to genetically modify ex vivo expanded NK cells to improve their tumor homing capacity and anti-tumor cytotoxic function.

EXAMPLE 5

Augmented NK Cell ADCC Against Multiple Myeloma Cells by Introduction of High-Affinity CD16-158V Receptor This example describes ADCC of NK cells expressing high-affinity CD16-158V and evaluation of ADCC against multiple myeloma cells contacted with daratumumab.

The multiple myeloma MM1S cells were counted and suspend to $1 \times 10^6$/ml, and transferred to 100 µl MM1S/well into a 96 well plate. The anti-CD38 antibody daratumumab was added to appropriate wells with MM1S (final concentration 10 µg/ml). The cells were incubated for 20 minutes at room temperature, and then washed twice to remove the antibody. The cells were resuspended in 100 µl medium and 100 µl NK cells were added to each well and incubated at 37 degrees for one hour. The cells were centrifuged and stained on ice for 15 minutes with anti-CD56, anti-CD3, anti-CD107a and the LIVE/DEAD marker Aqua. The cells were washed in PBS with 2 mM EDTA and 0.5% FCS. The stained cells were analyzed on a flow cytometer using the FLOWJO® software. Graphs are made in GRAPHPAD® PRISM.

Figure 5B:
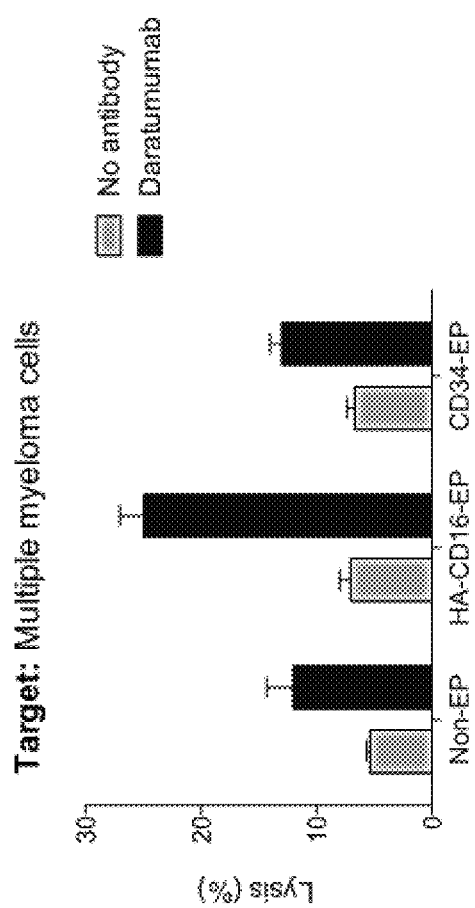
FIGS. 5A and 5B are a pair of graphs showing the effect of CD16 expression on NK cells.
Figure 5A:
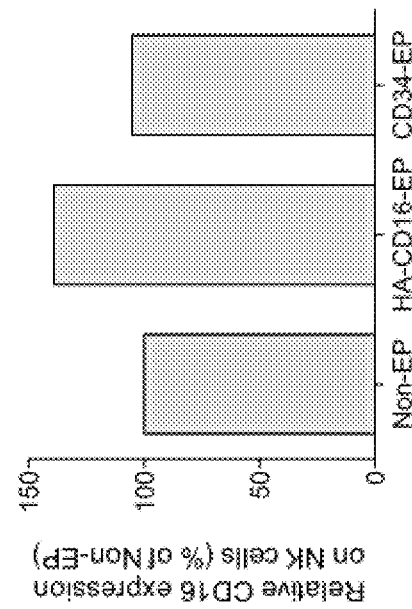

Electroporated NK cells maintained high cytotoxic function against K562 cells and multiple myeloma cells. NK cell killing of daratumumab-treated MM cells was substantially greater by NK cells expanded from donors homozygous for high affinity CD16 compared to those with low-affinity CD16. The resulting NK cells showed enhanced ADCC against daratumumab-coated MM cells by ex vivo expanded NK cells electroporated with mRNA coding for HA-CD16 (FIGS. 5A and 5B).

EXAMPLE 6

Treatment of Multiple Myeloma

A phase I clinical trial for relapsed MM patients who require therapy is initiated, treating up to 18 patients using a standard 3+3 enrollment scheme. A schematic diagram of an exemplary trial protocol is shown in FIG. 6.

NK cells are expanded from myeloma patients ex vivo using the methods described in Example 1. Patients are treated with daratumumab (8 mg/kg) weekly ×4 (same scheme as currently used for single therapy). Within six hours of the first two daratumumab infusions, patients receive an adoptive infusion of expanded NK cells transfected to express HA-CD16 (for example, as described in Examples 1 and 4). Prior to infusion, NK cells are treated with an anti-CD38 F(ab)2 (0.5-2 mg/ml in PBS) to protect them from daratumumab-mediated apoptosis.

Three cohorts receiving escalating numbers of NK cells are treated as follows:

Cohort 1=$1 \times 10^7$ NK cells/kg
Cohort 2=$5 \times 10^7$ NK cells/kg
Cohort 3=$1 \times 10^8$ NK cells/kg The primary endpoint of this trial is safety, with any grade ≥3 toxicity possibly or definitely related to the NK cell infusion considered a dose-limiting toxicity. The secondary endpoint is a clinical response. Patients are restaged 4 weeks after each treatment cycle and those showing disease regression as determined by >30% decline in bone marrow plasma cells or a reduction in the serum M spike and/or clonal serum free light chain levels of ≥25% are eligible to receive additional cycles of therapy.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of treating a subject with multiple myeloma, comprising:

obtaining a population of natural killer (NK) cells from the subject or a donor;

transfecting the population of NK cells with:

a heterologous nucleic acid molecule encoding a CD16 protein comprising a valine at amino acid position 158 of the mature CD16 protein; and a heterologous nucleic acid molecule encoding a CCR7 protein, thereby producing a population of modified NK cells;

blocking CD38 surface antigen of the population of modified NK cells by treating with a Fab or F(ab)2 fragment of an anti-CD38 monoclonal antibody to produce a population of CD38-blocked modified NK cells;

administering a composition comprising a monoclonal antibody to the subject, wherein the monoclonal antibody binds to cancer cells expressing CD38; and administering a composition comprising the CD38-blocked modified NK cells to the subject.

2. The method of claim 1, wherein the population of NK cells is expanded in vitro prior to transfection with the heterologous nucleic acid molecule.

3. The method of claim 1, wherein:

the nucleic acid molecule encoding the CD16 protein comprising a valine at amino acid position 158 of the mature CD16 protein encodes a protein comprising the amino acid sequence of SEQ ID NO: 4 or SEQ ID NO: 6, wherein the valine at amino acid position 158 of the mature CD16 protein corresponds to amino acid 212 of SEQ ID NO: 4 or amino acid 176 of SEQ ID NO: 6; and/or the nucleic acid molecule encoding the CD16 protein comprising a valine at amino acid position 158 of the mature CD16 protein comprises the nucleic acid sequence of SEQ ID NO: 3 or SEQ ID NO: 5.

4. The method of claim 1, wherein:

the nucleic acid molecule encoding the CCR7 protein encodes a protein comprising the amino acid sequence of SEQ ID NO: 9; and/or the nucleic acid molecule encoding the CCR7 protein comprises the nucleic acid sequence of SEQ ID NO: 8 or SEQ ID NO: 10.

5. The method of claim 1, wherein the monoclonal antibody is daratumumab.

6. The method of claim 1, wherein the composition comprising the CD38-blocked modified NK cells is administered to the subject after administering the composition comprising the monoclonal antibody to the subject.

7. The method of claim 6, wherein the composition comprising the CD38-blocked modified NK cells is administered to the subject about 1-8 hours after the composition comprising the monoclonal antibody is administered to the subject.

8. A method of treating a subject with lymphoma, comprising:

obtaining a population of natural killer (NK) cells from the subject or a donor;

transfecting the population of NK cells with:

a heterologous nucleic acid molecule encoding a CD16 protein comprising a valine at amino acid position 158 of the mature CD16 protein; and a heterologous nucleic acid molecule encoding a CCR7 protein, thereby producing a population of modified NK cells;

administering a composition comprising a monoclonal antibody to the subject, wherein the monoclonal antibody binds to cancer cells expressing CD20; and administering a composition comprising the modified NK cells to the subject.

9. The method of claim 8, wherein the population of NK cells is expanded in vitro prior to transfection with the heterologous nucleic acid molecule.

10. The method of claim 8, wherein:

the nucleic acid molecule encoding the CD16 protein comprising a valine at amino acid position 158 of the mature CD16 protein encodes a protein comprising the amino acid sequence of SEQ ID NO: 4 or SEQ ID NO: 6, wherein the valine at amino acid position 158 of the mature CD16 protein corresponds to amino acid 212 of SEQ ID NO: 4 or amino acid 176 of SEQ ID NO: 6; and/or the nucleic acid molecule encoding the CD16 protein comprising a valine at amino acid position 158 of the mature CD16 protein comprises the nucleic acid sequence of SEQ ID NO: 3 or SEQ ID NO: 5.

11. The method of claim 8, wherein:

the nucleic acid molecule encoding the CCR7 protein encodes a protein comprising the amino acid sequence of SEQ ID NO: 9; and/or the nucleic acid molecule encoding the CCR7 protein comprises the nucleic acid sequence of SEQ ID NO: 8 or SEQ ID NO: 10.

12. The method of claim 8, wherein the monoclonal antibody is rituximab, ofatumumab, veltuzumab, ibritumomab tiuxetan, obinutuzumab, ublituomab, tositumomab, or ocaratuzumab.

13. The method of claim 8, wherein the composition comprising the modified NK cells is administered to the subject after administering the composition comprising the monoclonal antibody to the subject.

14. The method of claim 13, wherein the composition comprising the modified NK cells is administered to the subject about 1-8 hours after the composition comprising the monoclonal antibody is administered to the subject.

* * * * *

SEQUENCE LISTING

```
<160> NUMBER OF SEQ ID NOS: 10

<210> SEQ ID NO 1
<211> LENGTH: 2406
<212> TYPE: DNA
<213> ORGANISM: Homo sapiens

<400> SEQUENCE: 1
gattctgtgt gtgtcctcag atgctcagcc acagaccttt gagggagtaa aggggggcaga      60 cccacccacc ttgcctccag gctctttcct tcctggtcct gttctatggt ggggctccct     120
tgccagactt cagactgaga agtcagatga agtttcaaga aaaggaaatt ggtgggtgac     180
agagatgggt ggaggggctg gggaaaggct gtttacttcc tcctgtctag tcggtttggt     240
ccctttaggg ctccggatat ctttggtgac ttgtccactc cagtgtggca tcatgtggca     300
gctgctcctc ccaactgctc tgctacttct agtttcagct ggcatgcgga ctgaagatct     360
cccaaaggct gtggtgttcc tggagcctca atggtacagg gtgctcgaga aggacagtgt     420
gactctgaag tgccagggag cctactcccc tgaggacaat tccacacagt ggtttcacaa     480
tgagagcctc atctcaagcc aggcctcgag ctacttcatt gacgctgcca cagtcgacga     540
cagtggagag tacaggtgcc agacaaacct ctccaccctc agtgacccgg tgcagctaga     600
agtccatatc ggctggctgt tgctccaggc ccctcggtgg gtgttcaagg aggaagaccc     660
tattcacctg aggtgtcaca gctggaagaa cactgctctg cataaggtca catatttaca     720
gaatggcaaa gcaggaagt attttcatca taattctgac ttctacattc caaaagccac     780
actcaaagac agcggctcct acttctgcag ggggcttttt gggagtaaaa atgtgtcttc     840
```

| | |
|---|---:|
| agagactgtg aacatcacca tcactcaagg tttggcagtg tcaaccatct catcattctt | 900 |
| tccacctggg taccaagtct cttttctgctt ggtgatggta ctccttttg cagtggacac | 960 |
| aggactatat ttctctgtga agacaaacat tcgaagctca acaagagact ggaaggacca | 1020 |
| taaatttaaa tggagaaagg accctcaaga caaatgaccc ccatcccatg ggggtaataa | 1080 |
| gagcagtagc agcagcatct ctgaacattt ctctggattt gcaaccccat catcctcagg | 1140 |
| cctctctaca agcagcagga aacatagaac tcagagccag atcccttatc caactctcga | 1200 |
| cttttccttg gtctccagtg aagggaaaa gcccatgatc ttcaagcagg gaagcccag | 1260 |
| tgagtagctg cattcctaga aattgaagtt tcagagctac acaaacactt tttctgtccc | 1320 |
| aaccgttccc tcacagcaaa gcaacaatac aggctaggga tggtaatcct ttaaacatac | 1380 |
| aaaaattgct cgtgttataa attacccagt ttagagggga aaaaaaaaca attattccta | 1440 |
| aataaatgga taagtagaat taatggttga ggcaggacca tacagagtgt ggggaactgct | 1500 |
| ggggatctag ggaattcagt gggaccaatg aaagcatggc tgagaaatag caggtagtcc | 1560 |
| aggatagtct aagggaggtg ttcccatctg agcccagaga taagggtgtc ttcctagaac | 1620 |
| attagccgta gtggaattaa caggaaatca tgagggtgac gtagaattga gtcttccagg | 1680 |
| ggactctatc agaactggac catctccaag tatataacga tgagtcctct taatgctagg | 1740 |
| agtagaaaat ggtcctagga aggggactga ggattgcggt ggggggtggg gtggaaaaga | 1800 |
| aagtacagaa caaaccctgt gtcactgtcc caagttgcta agtgaacaga actatctcag | 1860 |
| catcagaatg agaaagcctg agaagaaaga accaaccaca agcacacagg aaggaaagcg | 1920 |
| caggaggtga aaatgctttc ttggccaggg tagtaagaat tagaggttaa tgcagggact | 1980 |
| gtaaaaccac cttttctgct tcaatatcta attcctgtgt agctttgttc attgcattta | 2040 |
| ttaaacaaat gttgtataac caatactaaa tgtactactg agcttcgctg agttaagtta | 2100 |
| tgaaactttc aaatccttca tcatgtcagt tccaatgagg tggggatgga gaagacaatt | 2160 |
| gttgcttatg aaagaaagct ttagctgtct ctgttttgta agctttaagc gcaacatttc | 2220 |
| ttggttccaa taaagcattt tacaagatct tgcatgctac tcttagatag aagatgggaa | 2280 |
| aaccatggta ataaatatg aatgataaaa aaaaaaaaa aaaaaaaaa aaaaaaaaa | 2340 |
| aaaaaaaaaa aaaaaaaaa aaaaaaaaa aaaaaaaaa aaaaaaaaa aaaaaaaaa | 2400 |
| aaaaaa | 2406 |

<210> SEQ ID NO 2
<211> LENGTH: 290
<212> TYPE: PRT
<213> ORGANISM: Homo sapiens

<400> SEQUENCE: 2

Met Gly Gly Gly Ala Gly Glu Arg Leu Phe Thr Ser Ser Cys Leu Val
1               5                   10                  15

Gly Leu Val Pro Leu Gly Leu Arg Ile Ser Leu Val Thr Cys Pro Leu
            20                  25                  30

Gln Cys Gly Ile Met Trp Gln Leu Leu Leu Pro Thr Ala Leu Leu Leu
        35                  40                  45

Leu Val Ser Ala Gly Met Arg Thr Glu Asp Leu Pro Lys Ala Val Val
    50                  55                  60

Phe Leu Glu Pro Gln Trp Tyr Arg Val Leu Glu Lys Asp Ser Val Thr
65                  70                  75                  80

Leu Lys Cys Gln Gly Ala Tyr Ser Pro Glu Asp Asn Ser Thr Gln Trp
                85                  90                  95

```
Phe His Asn Glu Ser Leu Ile Ser Ser Gln Ala Ser Ser Tyr Phe Ile
                100                 105                 110

Asp Ala Ala Thr Val Asp Asp Ser Gly Glu Tyr Arg Cys Gln Thr Asn
            115                 120                 125

Leu Ser Thr Leu Ser Asp Pro Val Gln Leu Glu Val His Ile Gly Trp
        130                 135                 140

Leu Leu Leu Gln Ala Pro Arg Trp Val Phe Lys Glu Glu Asp Pro Ile
145                 150                 155                 160

His Leu Arg Cys His Ser Trp Lys Asn Thr Ala Leu His Lys Val Thr
                165                 170                 175

Tyr Leu Gln Asn Gly Lys Gly Arg Lys Tyr Phe His His Asn Ser Asp
            180                 185                 190

Phe Tyr Ile Pro Lys Ala Thr Leu Lys Asp Ser Gly Ser Tyr Phe Cys
        195                 200                 205

Arg Gly Leu Phe Gly Ser Lys Asn Val Ser Ser Glu Thr Val Asn Ile
    210                 215                 220

Thr Ile Thr Gln Gly Leu Ala Val Ser Thr Ile Ser Ser Phe Phe Pro
225                 230                 235                 240

Pro Gly Tyr Gln Val Ser Phe Cys Leu Val Met Val Leu Leu Phe Ala
                245                 250                 255

Val Asp Thr Gly Leu Tyr Phe Ser Val Lys Thr Asn Ile Arg Ser Ser
            260                 265                 270

Thr Arg Asp Trp Lys Asp His Lys Phe Lys Trp Arg Lys Asp Pro Gln
        275                 280                 285

Asp Lys
    290

<210> SEQ ID NO 3
<211> LENGTH: 2406
<212> TYPE: DNA
<213> ORGANISM: Homo sapiens

<400> SEQUENCE: 3
gattctgtgt gtgtcctcag atgctcagcc acagaccttt gagggagtaa aggggggcaga      60 cccacccacc ttgcctccag gctctttcct tcctggtcct gttctatggt ggggctccct     120
tgccagactt cagactgaga agtcagatga agtttcaaga aaaggaaatt ggtgggtgac     180
agagatgggt ggaggggctg gggaaaggct gtttacttcc tcctgtctag tcggtttggt     240
ccctttaggg ctccggatat ctttggtgac ttgtccactc cagtgtggca tcatgtggca     300
gctgctcctc ccaactgctc tgctacttct agtttcagct ggcatgcgga ctgaagatct     360
cccaaaggct gtggtgttcc tggagcctca atggtacagg gtgctcgaga aggacagtgt     420
gactctgaag tgccagggag cctactcccc tgaggacaat tccacacagt ggtttcacaa     480
tgagagcctc atctcaagcc aggcctcgag ctacttcatt gacgctgcca cagtcgacga     540
cagtggagag tacaggtgcc agacaaacct ctccaccctc agtgacccgg tgcagctaga     600
agtccatatc ggctggctgt tgctccaggc ccctcggtgg gtgttcaagg aggagaccc     660 tattcacctg aggtgtcaca gctggaagaa cactgctctg cataaggtca catatttaca     720
gaatggcaaa ggcaggaagt attttcatca taattctgac ttctacattc caaaagccac     780
actcaaagac agcggctcct acttctgcag ggggcttgtt gggagtaaaa atgtgtcttc     840
agagactgtg aacatcacca tcactcaagg tttggcagtg tcaaccatct catcattctt     900
tccacctggg taccaagtct ctttctgctt ggtgatggta ctcctttttg cagtggacac     960
```

```
aggactatat ttctctgtga agacaaacat tcgaagctca acaagagact ggaaggacca      1020
taaatttaaa tggagaaagg accctcaaga caaatgaccc ccatcccatg ggggtaataa      1080
gagcagtagc agcagcatct ctgaacattt ctctggattt gcaaccccat catcctcagg      1140
cctctctaca agcagcagga aacatagaac tcagagccag atcccttatc caactctcga      1200
cttttccttg gtctccagtg aagggaaaa gcccatgatc ttcaagcagg aagccccag       1260 tgagtagctg cattcctaga aattgaagtt tcagagctac acaaacactt tttctgtccc      1320
aaccgttccc tcacagcaaa gcaacaatac aggctaggga tggtaatcct ttaaacatac      1380
aaaaattgct cgtgttataa attacccagt ttagagggga aaaaaaaaca attattccta      1440
aataaatgga taagtagaat taatggttga ggcaggacca tacagagtgt gggaactgct      1500
ggggatctag ggaattcagt gggaccaatg aaagcatggc tgagaaatag caggtagtcc      1560
aggatagtct aagggaggtg ttcccatctg agcccagaga taagggtgtc ttcctagaac      1620
attagccgta gtggaattaa caggaaatca tgagggtgac gtagaattga gtcttccagg      1680
ggactctatc agaactggac catctccaag tatataacga tgagtcctct taatgctagg      1740
agtagaaaat ggtcctagga aggggactga ggattgcggt gggggtggg gtggaaaaga       1800 aagtacagaa caaaccctgt gtcactgtcc caagttgcta agtgaacaga actatctcag      1860
catcagaatg agaaagcctg agaagaaaga accaaccaca agcacacagg aaggaaagcg      1920
caggaggtga aaatgctttc ttggccaggg tagtaagaat tagaggttaa tgcagggact      1980
gtaaaaccac cttttctgct tcaatatcta attcctgtgt agctttgttc attgcattta      2040
ttaaacaaat gttgtataac caatactaaa tgtactactg agcttcgctg agttaagtta      2100
tgaaactttc aaatccttca tcatgtcagt tccaatgagg tggggatgga gaagacaatt      2160
gttgcttatg aaagaaagct ttagctgtct ctgttttgta agctttaagc gcaacatttc      2220
ttggttccaa taaagcattt tacaagatct tgcatgctac tcttagatag aagatgggaa      2280
aaccatggta ataaaatatg aatgataaaa aaaaaaaaaa aaaaaaaaaa aaaaaaaaaa      2340
aaaaaaaaaa aaaaaaaaaa aaaaaaaaaa aaaaaaaaaa aaaaaaaaaa aaaaaaaaaa      2400
aaaaaa                                                                2406

<210> SEQ ID NO 4
<211> LENGTH: 290
<212> TYPE: PRT
<213> ORGANISM: Homo sapiens

<400> SEQUENCE: 4

Met Gly Gly Gly Ala Gly Glu Arg Leu Phe Thr Ser Ser Cys Leu Val
1               5                   10                  15

Gly Leu Val Pro Leu Gly Leu Arg Ile Ser Leu Val Thr Cys Pro Leu
            20                  25                  30

Gln Cys Gly Ile Met Trp Gln Leu Leu Leu Pro Thr Ala Leu Leu Leu
        35                  40                  45

Leu Val Ser Ala Gly Met Arg Thr Glu Asp Leu Pro Lys Ala Val Val
    50                  55                  60

Phe Leu Glu Pro Gln Trp Tyr Arg Val Leu Glu Lys Asp Ser Val Thr
65                  70                  75                  80

Leu Lys Cys Gln Gly Ala Tyr Ser Pro Glu Asp Asn Ser Thr Gln Trp
                85                  90                  95

Phe His Asn Glu Ser Leu Ile Ser Ser Gln Ala Ser Ser Tyr Phe Ile
            100                 105                 110
```

Asp Ala Ala Thr Val Asp Asp Ser Gly Glu Tyr Arg Cys Gln Thr Asn
        115                 120                 125

Leu Ser Thr Leu Ser Asp Pro Val Gln Leu Glu Val His Ile Gly Trp
    130                 135                 140

Leu Leu Leu Gln Ala Pro Arg Trp Val Phe Lys Glu Glu Asp Pro Ile
145                 150                 155                 160

His Leu Arg Cys His Ser Trp Lys Asn Thr Ala Leu His Lys Val Thr
                165                 170                 175

Tyr Leu Gln Asn Gly Lys Gly Arg Lys Tyr Phe His His Asn Ser Asp
            180                 185                 190

Phe Tyr Ile Pro Lys Ala Thr Leu Lys Asp Ser Gly Ser Tyr Phe Cys
        195                 200                 205

Arg Gly Leu Val Gly Ser Lys Asn Val Ser Ser Glu Thr Val Asn Ile
    210                 215                 220

Thr Ile Thr Gln Gly Leu Ala Val Ser Thr Ile Ser Ser Phe Phe Pro
225                 230                 235                 240

Pro Gly Tyr Gln Val Ser Phe Cys Leu Val Met Val Leu Leu Phe Ala
                245                 250                 255

Val Asp Thr Gly Leu Tyr Phe Ser Val Lys Thr Asn Ile Arg Ser Ser
            260                 265                 270

Thr Arg Asp Trp Lys Asp His Lys Phe Lys Trp Arg Lys Asp Pro Gln
        275                 280                 285

Asp Lys
    290

<210> SEQ ID NO 5
<211> LENGTH: 765
<212> TYPE: RNA
<213> ORGANISM: Homo sapiens

<400> SEQUENCE: 5
auguggcagc ugcuccuccc aacugcucug cuacuucuag uuucagcugg caugcggacu    60
gaagaucucc caaaggcugu ggguguuccug gagccucaau gguacagggu gcucgagaag   120
gacaguguga cucugaagug ccagggagcc uacuccccug aggacaauuc cacacagugg   180
uuucacaaug agagccucau ucaagccag gccucgagcu acuucauuga cgcugccaca   240
gucgacgaca guggagagua caggugccag acaaaccucu ccacccucag ugacccggug   300
cagcuagaag uccauaucgg cuggcuguug uccaggccc cucggugggu guucaaggag   360
gaagacccua uuaccugag gugucacagc uggaagaaca cugcucugca uaaggucaca   420
uauuuacaga auggcaaagg caggaaguau uuucaucaua auucugacuu cuacauucca   480
aaagccacac ucaagacag cggcuccuac uucugcaggg ggcuuguggg aguaaaaau    540 gugucuucag agacugugaa caucaccauc acucaagguu uggcagugu aaccaucuca   600 ucauucuuuc caccggguaa ccaagucucu uucugcuugg ugaugguacu ccuuuugca   660 guggacacag gacuauauuu cucugugaag acaaacauuc gaagcuacaa aagagacugg   720
aaggaccaua aauuaaaug gagaaaggac ccucaagaca auga                    765

<210> SEQ ID NO 6
<211> LENGTH: 254
<212> TYPE: PRT
<213> ORGANISM: Homo sapiens

<400> SEQUENCE: 6

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50              55                  60

Ser His Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 7
<211> LENGTH: 1158
<212> TYPE: RNA
<213> ORGANISM: Homo sapiens

<400> SEQUENCE: 7
augcuggucc gcaggggcgc gcgcgcaggg cccaggaugc cgcggggcug gaccgcgcuu    60
ugcuugcuga guuugcugcc uucggguuc augagucuug acaacaacgg uacugcuacc   120
ccagaguuac cuacccaggg aacauuuuca aauguuucua caaauguauc uaccaagaa   180
acuacaacac cuaguacccu uggaaguacc agccugcacc cuguguucuca acauggcaau   240
gaggccacaa caaacaucac agaaacgaca gucaaauuca caucuaccuc ugugauaacc   300
ucaguuuaug aaacacaaa cucuucuguc cagucacaga ccucuguaau cagcacagug   360
uucaccaccc cagccaacgu uucaacucca gagacaaccu ugaagccuag ccugucaccu   420
ggaaauguuu cagaccuuuc aaccacuagc acuagccuug caacaucucc cacuaaaccc   480
uauacaucau cuucuccuau ccuaagugac aucaaggcag aaaucaaaug uucaggcauc   540
agagaaguga aauugacuca gggcaucugc cuggagcaaa auaagaccuc cagcugugcg   600
gaguuuaaga aggacagggg agagggccug gcccgagugc ugugugggga ggagcaggcu   660
gaugcugaug cuggggccca gguaugcucc cugcuccuug cccagucuga ggugaggccu   720

-continued

| | |
|---|---|
| cagugucuac ugcuggucuu ggccaacaga acagaaauuu ccagcaaacu ccaacuuaug | 780 |
| aaaaagcacc aaucugaccu gaaaaagcug gggauccuag auuucacuga gcaagauguu | 840 |
| gcaagccacc agagcuauuc ccaaaagacc cugauugcac ugucaccuc gggagcccug | 900 |
| cuggcugucu ugggcaucac uggcuauuuc cugaugaauc gccgcagcug gagccccaca | 960 |
| ggagaaaggc ugggcgaaga cccuuauuac acggaaaacg guggaggcca gggcuauagc | 1020 |
| ucaggaccug ggaccucccc ugaggcucag ggaaaggcca gugugaaccg aggggcucag | 1080 |
| gaaaacggga ccggccaggc caccuccaga aacggccauu cagcaagaca cacguggug | 1140 |
| gcugauaccg aauuguaa | 1158 |

<210> SEQ ID NO 8
<211> LENGTH: 2207
<212> TYPE: DNA
<213> ORGANISM: Homo sapiens

<400> SEQUENCE: 8

| | |
|---|---|
| cacttcctcc ccagacaggg gtagtgcgag gccgggcaca gccttcctgt gtggttttac | 60 |
| cgcccagaga gcgtcatgga cctggggaaa ccaatgaaaa gcgtgctggt ggtggctctc | 120 |
| cttgtcattt tccaggtatg cctgtgtcaa gatgaggtca cggacgatta catcggagac | 180 |
| aacaccacag tggactacac tttgttcgag tctttgtgct ccaagaagga cgtgcggaac | 240 |
| tttaaagcct ggttcctccc tatcatgtac tccatcattt gtttcgtggg cctactgggc | 300 |
| aatgggctgg tcgtgttgac ctatatctat ttcaagaggc tcaagaccat gaccgatacc | 360 |
| tacctgctca acctggcggt ggcagacatc ctcttcctcc tgacccttcc cttctgggcc | 420 |
| tacagcgcgg ccaagtcctg ggtcttcggt gtccactttt gcaagctcat ctttgccatc | 480 |
| tacaagatga gcttcttcag tggcatgctc ctacttcttt gcatcagcat tgaccgctac | 540 |
| gtggccatcg tccaggctgt ctcagctcac cgccaccgtg cccgcgtcct tctcatcagc | 600 |
| aagctgtcct gtgtgggcat ctggatacta gccacagtgc tctccatccc agagctcctg | 660 |
| tacagtgacc tccagaggag cagcagtgag caagcgatgc gatgctctct catcacagag | 720 |
| catgtggagg cctttatcac catccaggtg gcccagatgt tgatcggctt tctggtcccc | 780 |
| ctgctggcca tgagcttctg ttaccttgtc atcatccgca ccctgctcca ggcacgcaac | 840 |
| tttgagcgca acaaggccat caaggtgatc atcgctgtgg tcgtggtctt catagtcttc | 900 |
| cagctgccct acaatgggt ggtcctggcc cagacggtgg ccaacttcaa catcaccagt | 960 |
| agcacctgtg agctcagtaa gcaactcaac atcgcctacg acgtcaccta cagcctggcc | 1020 |
| tgcgtccgct gctgcgtcaa cccctttctt gtacgccttc tcggcgtcaa gttccgcaac | 1080 |
| gatctcttca gctcttcaa ggacctgggc tgcctcagcc aggagcagct ccggcagtgg | 1140 |
| tcttcctgtc ggcacatccg gcgctcctcc atgagtgtgg aggccgagac caccaccacc | 1200 |
| ttctccccat aggcgactct tctgcctgga ctagaggac ctctcccagg gtccctgggg | 1260 |
| tggggatagg gagcagatgc aatgactcag gacatccccc cgccaaaagc tgctcaggga | 1320 |
| aaagcagctc tccctcaga gtgcaagccc ctgctccaga agatagcttc acccccaatcc | 1380 |
| cagctacctc aaccaatgcc aaaaaagac agggctgata agctaacacc agacagacaa | 1440 |
| cactgggaaa cagaggctat tgtcccctaa accaaaaact gaaagtgaaa gtccagaaac | 1500 |
| tgttcccacc tgctggagtg aaggggccaa ggagggtgag tgcaagggggc gtgggagtgg | 1560 |
| cctgaagagt cctctgaatg aaccttctgg cctcccacag actcaaatgc tcagaccagc | 1620 |

```
tcttccgaaa accaggcctt atctccaaga ccagagatag tggggagact tcttggcttg    1680
gtgaggaaaa gcggacatca gctggtcaaa caaactctct gaaccccctcc ctccatcgtt   1740 ttcttcactg tcctccaagc cagcgggaat ggcagctgcc acgccgccct aaaagcacac    1800
tcatcccctc acttgccgcg tcgcctcccc aggctctcaa caggggagag tgtggtgttt    1860
cctgcaggcc aggccagctg cctccgcgtg atcaaagcca cactctgggc tccagagtgg    1920
ggatgacatg cactcagctc ttggctccac tgggatggga ggagaggaca agggaaatgt    1980
caggggcggg gagggtgaca gtggccgccc aaggcccacg agcttgttct tgttctttg     2040 tcacagggac tgaaaacctc tcctcatgtt ctgctttcga ttcgttaaga gagcaacatt    2100
ttacccacac acagataaag ttttcccttg aggaacaac agctttaaaa gaaaagaaa      2160 aaaaagtct ttggtaaatg gcaaaaaaaa aaaaaaaaa aaaaaaa                    2207
```

<210> SEQ ID NO 9
<211> LENGTH: 378
<212> TYPE: PRT
<213> ORGANISM: Homo sapiens

<400> SEQUENCE: 9

```
Met Asp Leu Gly Lys Pro Met Lys Ser Val Leu Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270
```

```
Ile Val Phe Gln Leu Pro Tyr Asn Gly Val Val Leu Ala Gln Thr Val
            275                 280                 285

Ala Asn Phe Asn Ile Thr Ser Ser Thr Cys Glu Leu Ser Lys Gln Leu
        290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
    370                 375

<210> SEQ ID NO 10
<211> LENGTH: 1137
<212> TYPE: RNA
<213> ORGANISM: Homo sapiens

<400> SEQUENCE: 10
auggaccugg ggaaaccaau gaaaagcgug cuggugguag cucuccuugu cauuuccag      60 guaugccugu gucaagauga ggucacggac gauuacaucg agacaacac cacaguggac    120 uacacuuugu ucgagucuuu gugcuccaag aaggacgugc ggaacuuuaa agccugguuc   180
cucccuauca uguacccau cauuuguuuc gugggccuac ugggcaaugg gcuggucgug    240
uugaccuaua ucuauuucaa gaggcucaag accaugaccg auaccuaccu gcucaaccug   300
gcgguggcag acauccucuu ccuccugacc cuucccuucu gggccuacag cgcggccaag   360 uccuggggucu ucgguguccaa cuuuugcaag cucaucuuug ccaucuacaa gaugagcuuc  420
uucaguggca ugcuccuacu ucuuugcauc agcauugacc gcuacguggc caucguccag   480
gcugucucag cucaccgcca ccgugcccgc guccuucuca ucagcaagcu guccugugug   540
ggcaucugga uacuagccac agugcucucc aucccagagc uccuguacag ugaccuccag   600
aggagcagca gugagcaagc gaugcgaugc ucucucauca cagagcaugu ggaggccuuu   660
aucaccaucc agguggccca gauggugauc ggcuuucugg uccccccugcu ggccaugagc   720 uucuguuacc uugucaucau ccgcacccug uccaggcac gcaacuuuga gcgcaacaag   780
gccaucaagg ugaucaucgc uguggucgug gucuucauag ucuuccagcu gcccuacaau   840
ggggugguuc uggcccagac gguggccaac uucaacauca ccaguagcac cugugagcuc   900
aguaagcaac ucaacaucgu cuacgacguc accuacagcc uggccugcgu ccgcugcugc   960
gucaacccuu ucuuguacgc cuucaucggc gucaaguucc gcaacgaucu cuucaagcuc  1020
uucaaggacc uggggcugccu cagccaggag cagcuccggc aguggucuuc cugucggcac  1080
auccggcgcu ccuccaugag uguggaggcc gagaccacca ccaccuucuc cccauag     1137
```